(12) United States Patent
Myung

(10) Patent No.: US 11,439,523 B2
(45) Date of Patent: Sep. 13, 2022

(54) STENT

(71) Applicant: BCM Co., Ltd., Gyeonggi-do (KR)

(72) Inventor: Byung Cheol Myung, Gyeonggi-do (KR)

(73) Assignee: BCM Co., Ltd., Gyeonggi-do (KR)

( * ) Notice: Subject to any disclaimer, the term of this patent is extended or adjusted under 35 U.S.C. 154(b) by 252 days.

(21) Appl. No.: 16/825,376

(22) Filed: Mar. 20, 2020

(65) Prior Publication Data

US 2020/0315821 A1 Oct. 8, 2020

(30) Foreign Application Priority Data

Apr. 2, 2019 (KR) .................. 10-2019-0038647

(51) Int. Cl.
*A61F 2/852* (2013.01)
*A61F 2/90* (2013.01)
*A61F 2/848* (2013.01)
*A61F 2/82* (2013.01)
*A61F 2/07* (2013.01)

(52) U.S. Cl.
CPC .............. *A61F 2/852* (2013.01); *A61F 2/848* (2013.01); *A61F 2/90* (2013.01); *A61F 2002/072* (2013.01); *A61F 2002/828* (2013.01); *A61F 2002/8486* (2013.01); *A61F 2210/0014* (2013.01); *A61F 2220/0008* (2013.01); *A61F 2220/0075* (2013.01); *A61F 2250/0039* (2013.01); *A61F 2250/0063* (2013.01)

(58) Field of Classification Search
CPC .. A61F 2/852; A61F 2/848; A61F 2/90; A61F 2/86; A61F 2002/072; A61F 2002/828; A61F 2002/8486
See application file for complete search history.

(56) References Cited

U.S. PATENT DOCUMENTS

| 2009/0192588 A1* | 7/2009 | Shin .................. A61F 2/852 623/1.15 |
| 2019/0000606 A1* | 1/2019 | Shu .................... A61F 2/97 |

FOREIGN PATENT DOCUMENTS

| KR | 10-2010-0045211 | 5/2010 |
| KR | 10-2010-0122905 | 11/2010 |
| KR | 10-2011-0125783 | 11/2011 |

* cited by examiner

*Primary Examiner* — Suba Ganesan
(74) *Attorney, Agent, or Firm* — IP & T Group LLP

(57) ABSTRACT

A stent having an improved anti-sliding function is proposed. The stent includes an inner stent and a pair of outer stents that have undergone heat treatment and have several spaces formed by weaving or crossing wires made of a superelastic shape memory alloy in a hollow cylindrical net shape, in which each of the outer stents is shorter than the inner stent and has an enlarged section having a diameter larger than the inner stent and a bending section formed by bending inward a side of the enlarged section; and the pair of outer stents are fitted on both ends of the inner stent such that the enlarged sections of the outer stents face each other, and spaces of the inner stent and spaces of the bending sections of the outer stents are connected by a connection thread, whereby a space section is defined between the inner stent and the outer stents.

12 Claims, 42 Drawing Sheets

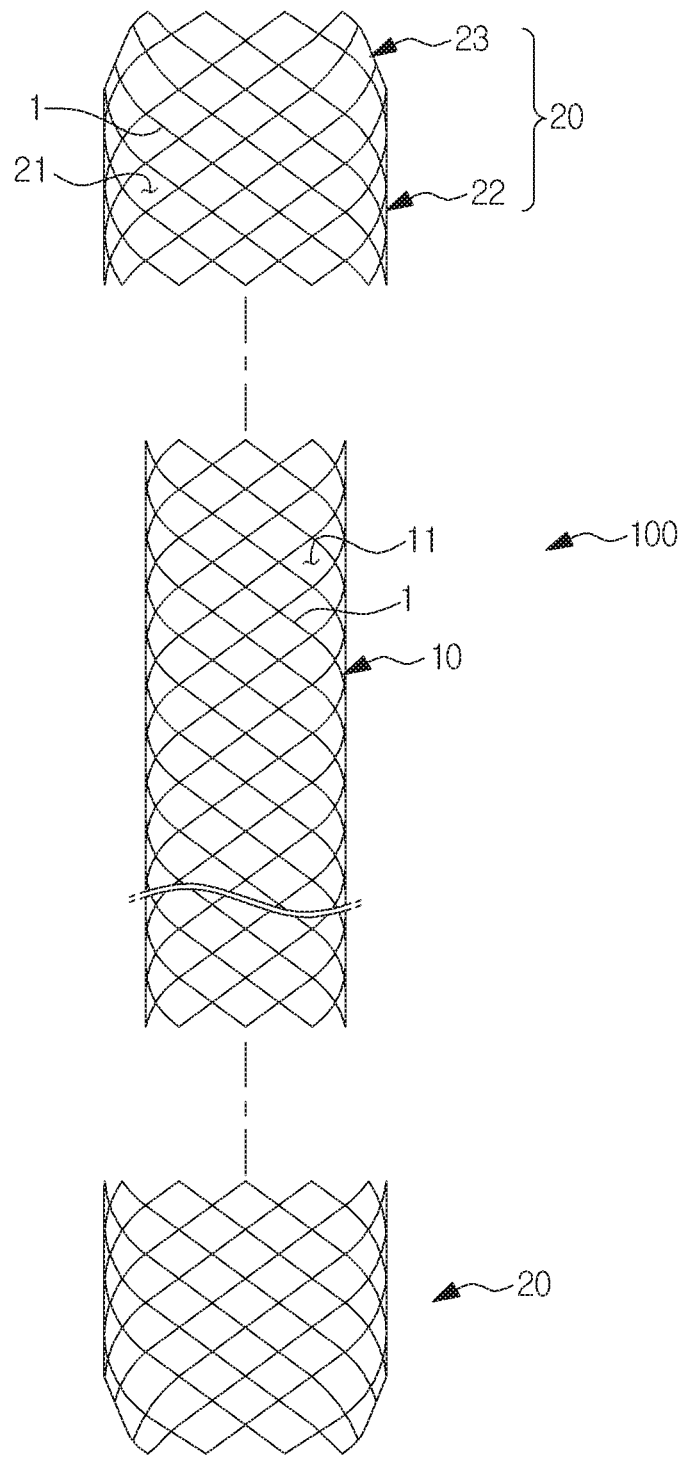
[FIG. 1]

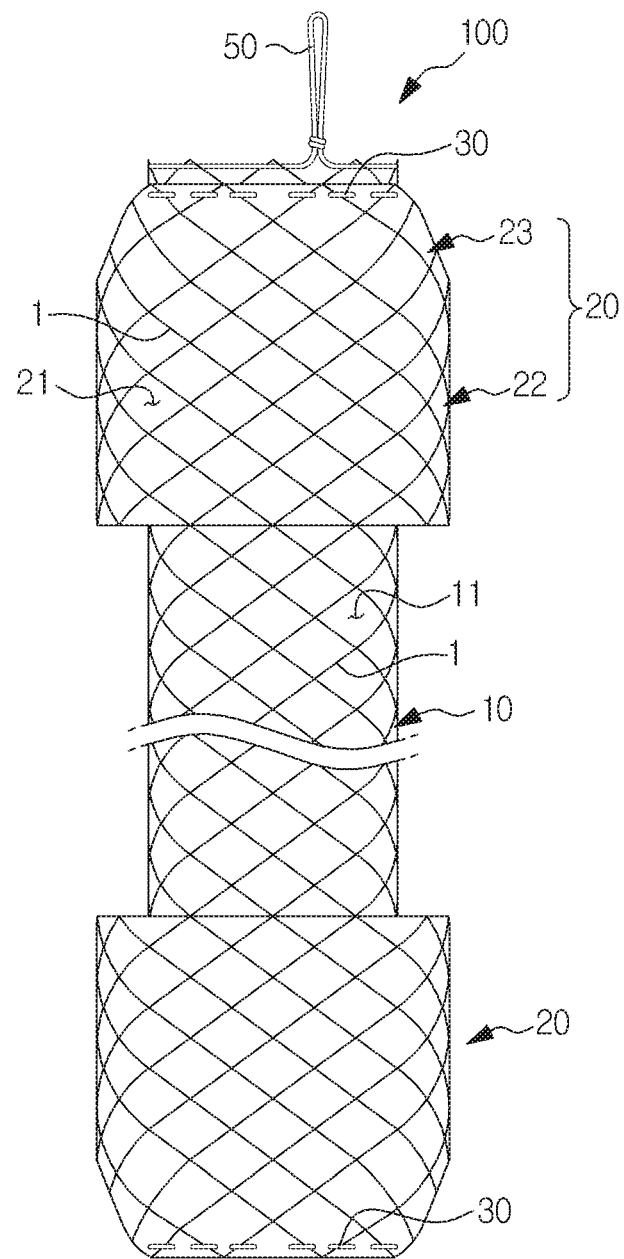
[FIG. 2A]

[FIG. 2B]
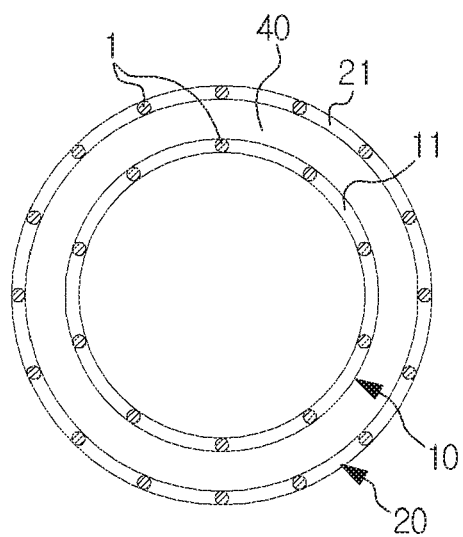
[FIG. 2C]
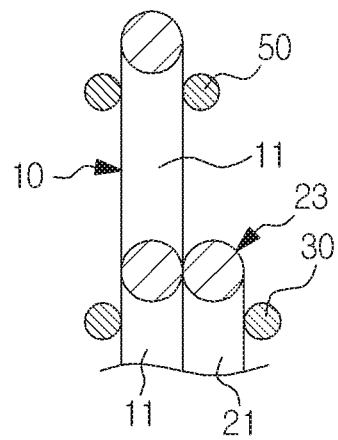

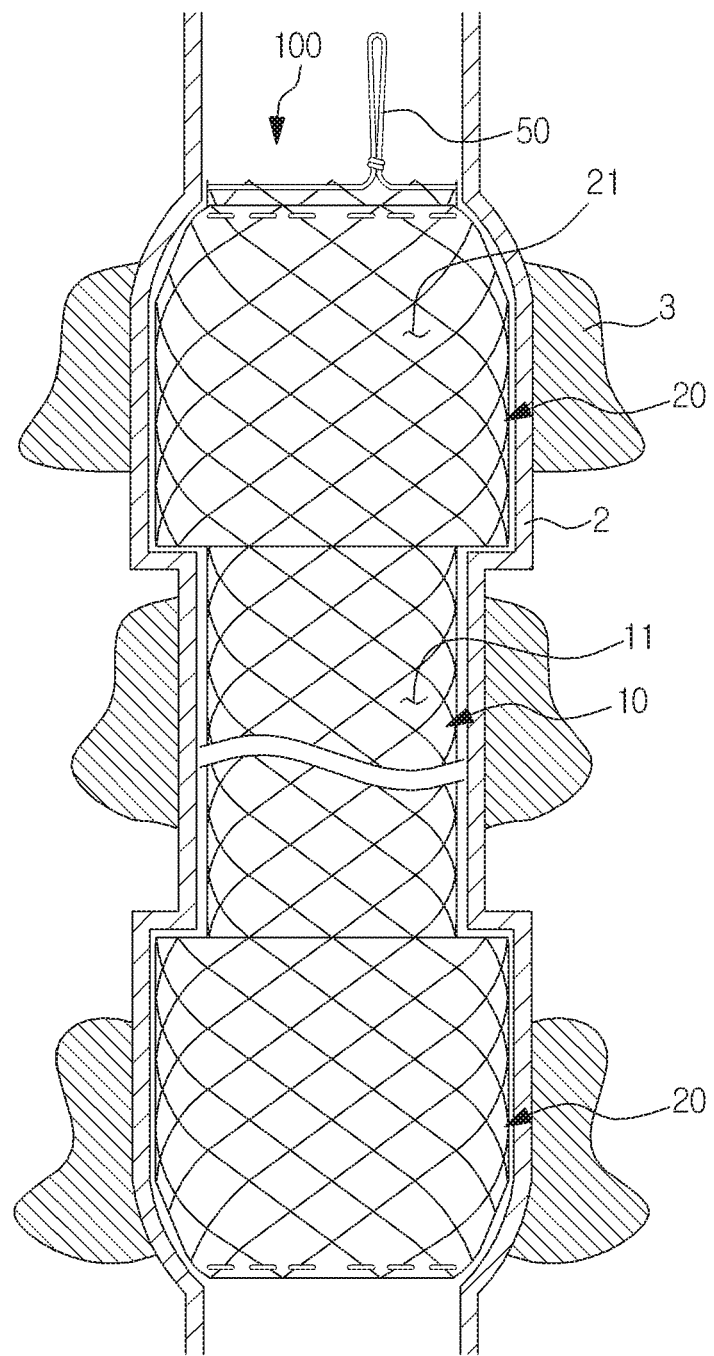
[FIG. 3A]

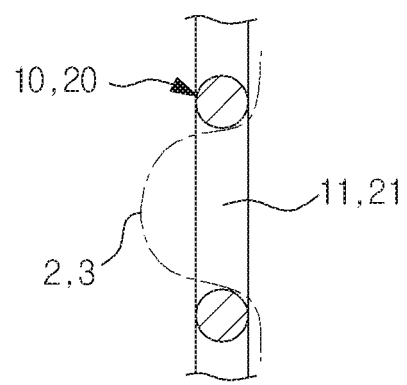
[FIG. 3B]

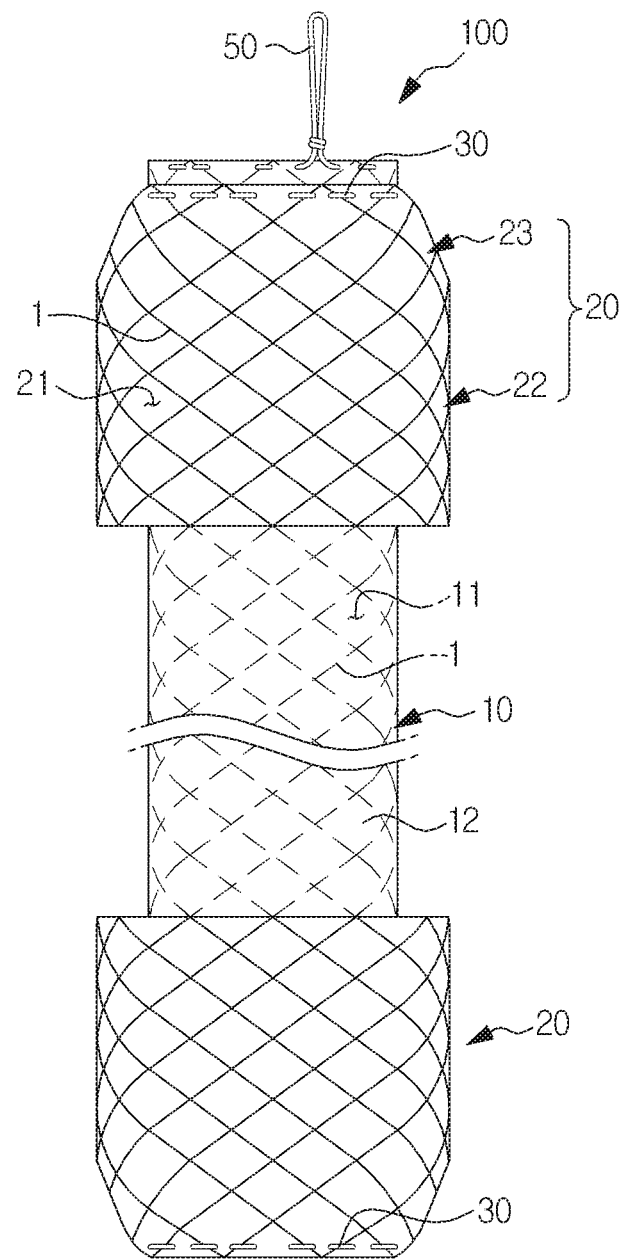
[FIG. 4A]

[FIG. 4B]
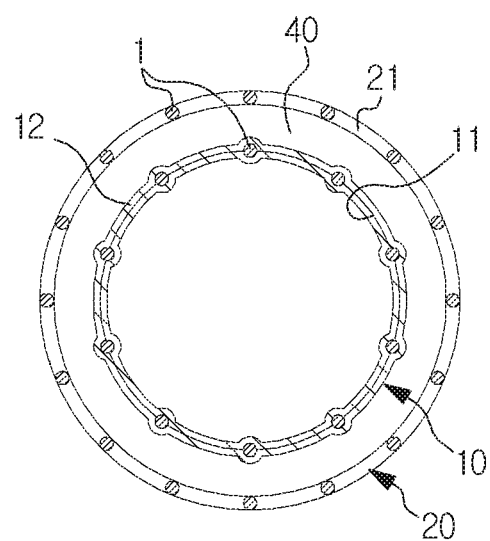
[FIG. 4C]
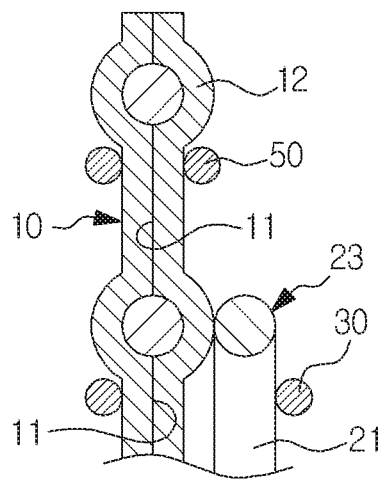

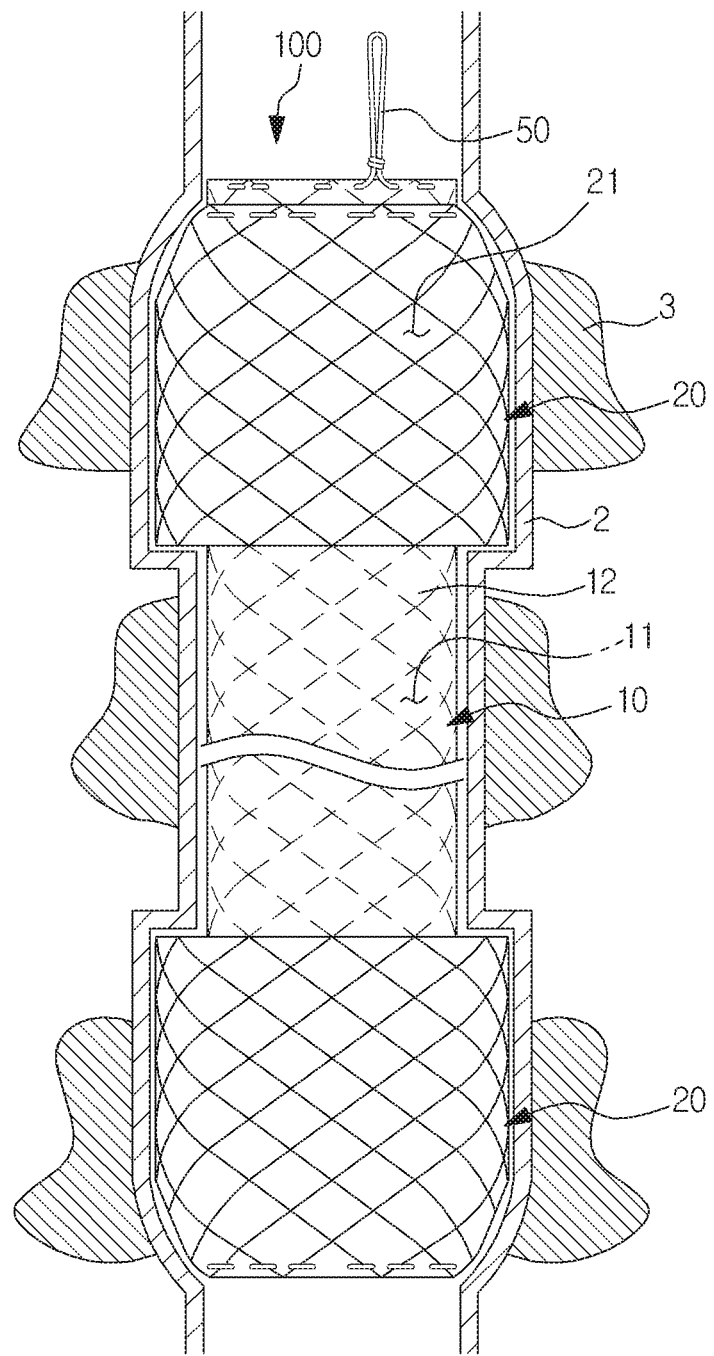
[FIG. 5A]

[FIG. 5B]
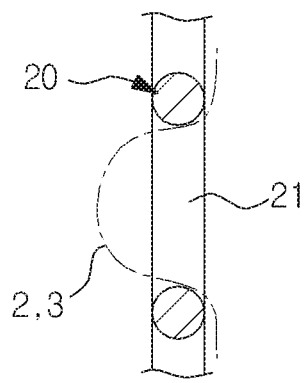
[FIG. 5C]
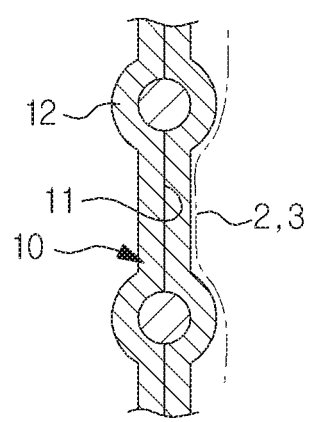

[FIG. 6A]
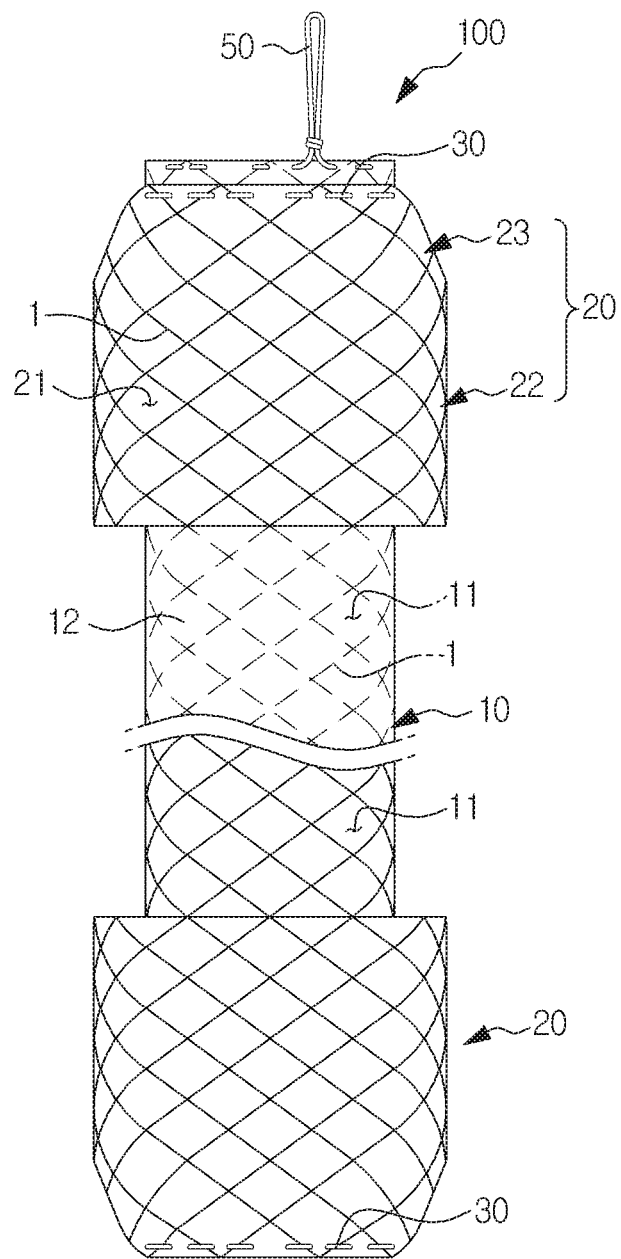

[FIG. 6B]
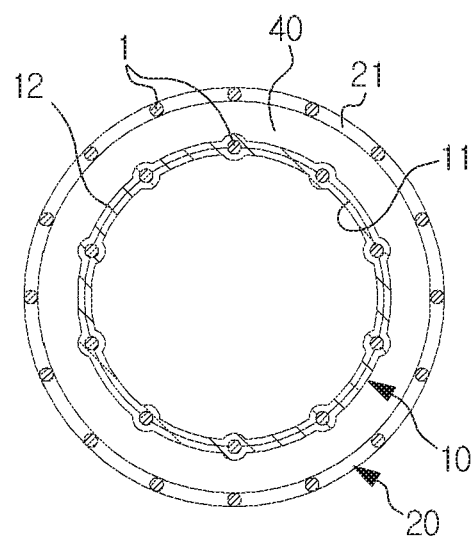
[FIG. 6C]
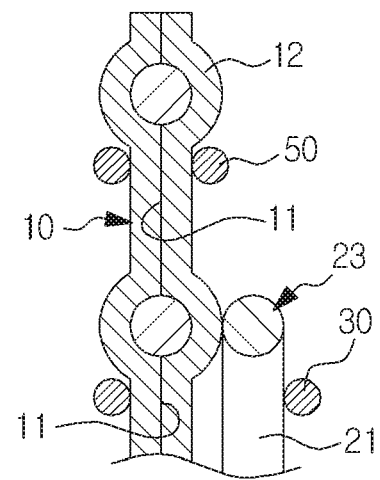

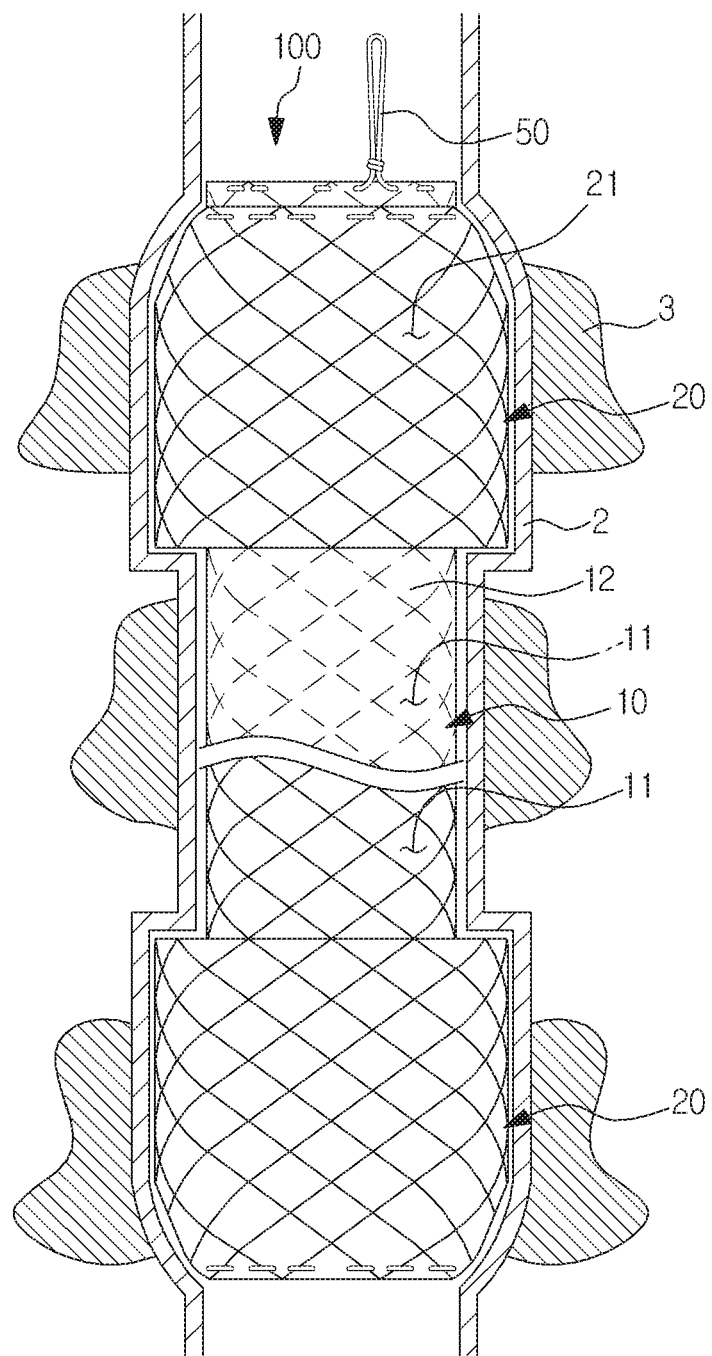
[FIG. 7A]

[FIG. 7B]
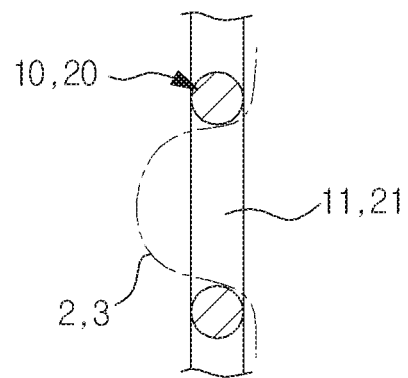
[FIG. 7C]
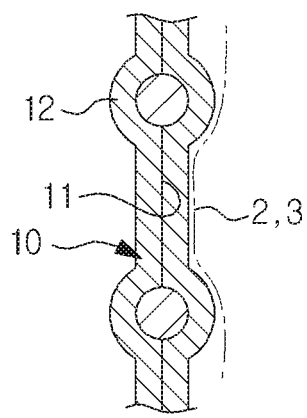

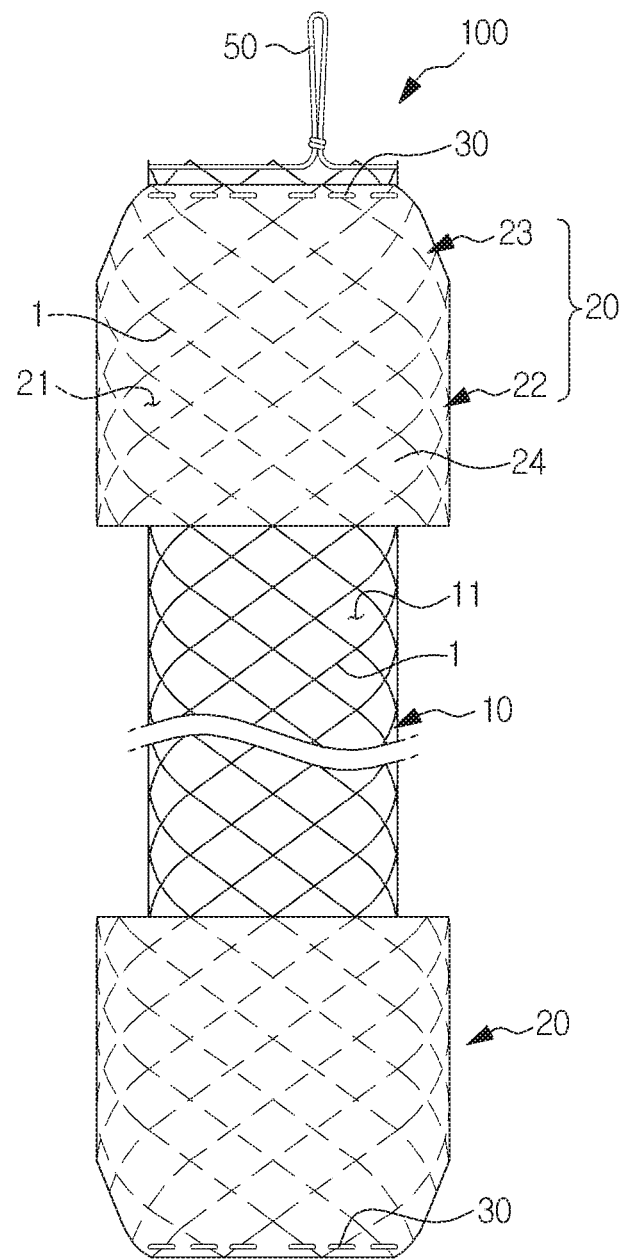
[FIG. 8A]

[FIG. 8B]
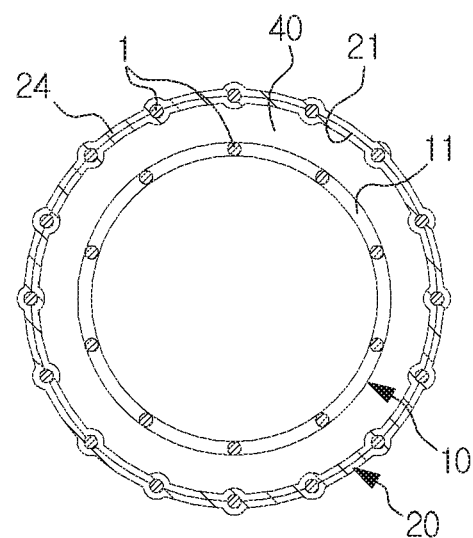
[FIG. 8C]
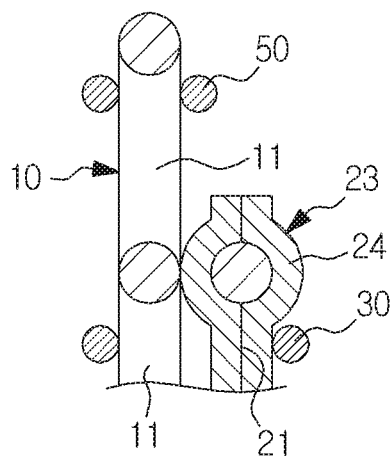

[FIG. 9A]
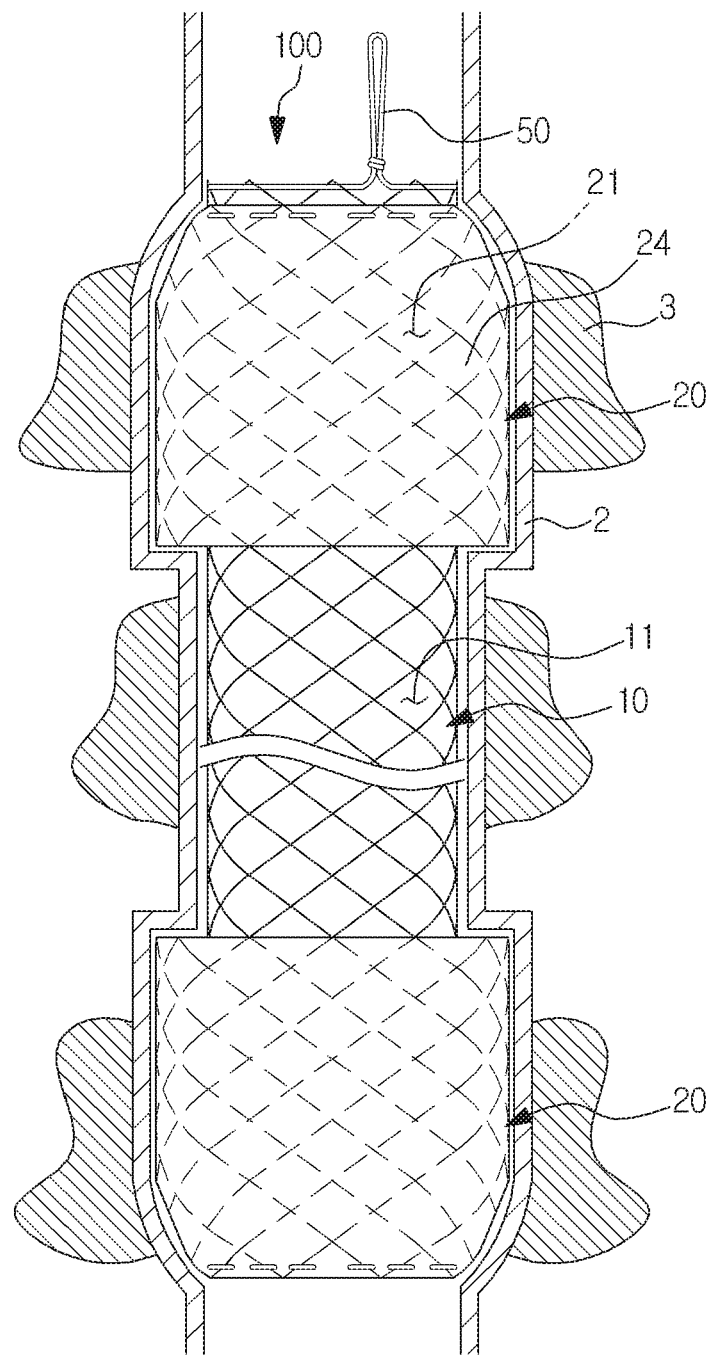

[FIG. 9B]
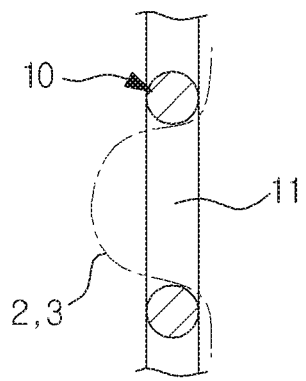
[FIG. 9C]
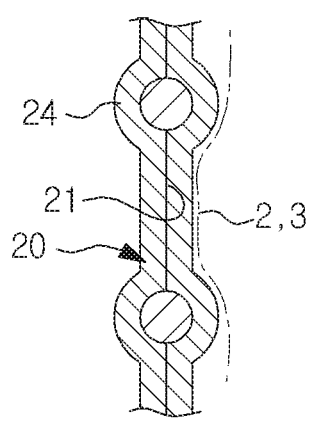

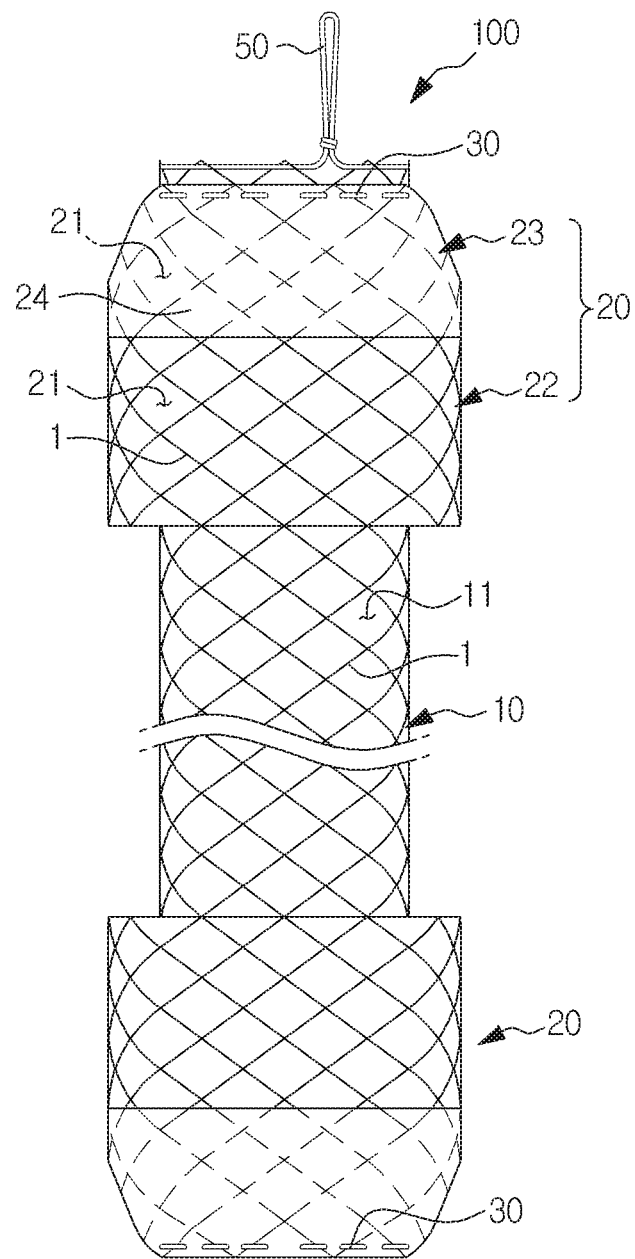
[FIG. 10A]

[FIG. 10B]
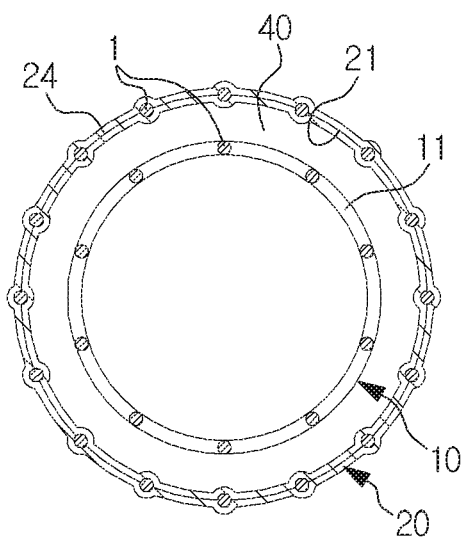
[FIG. 10C]
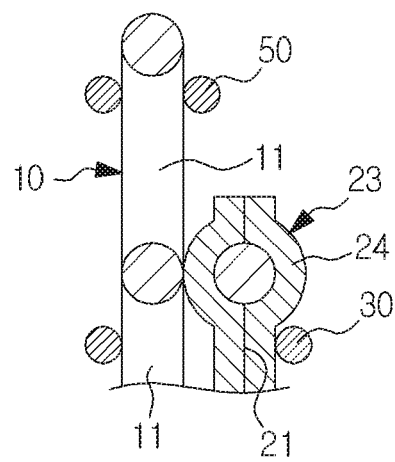

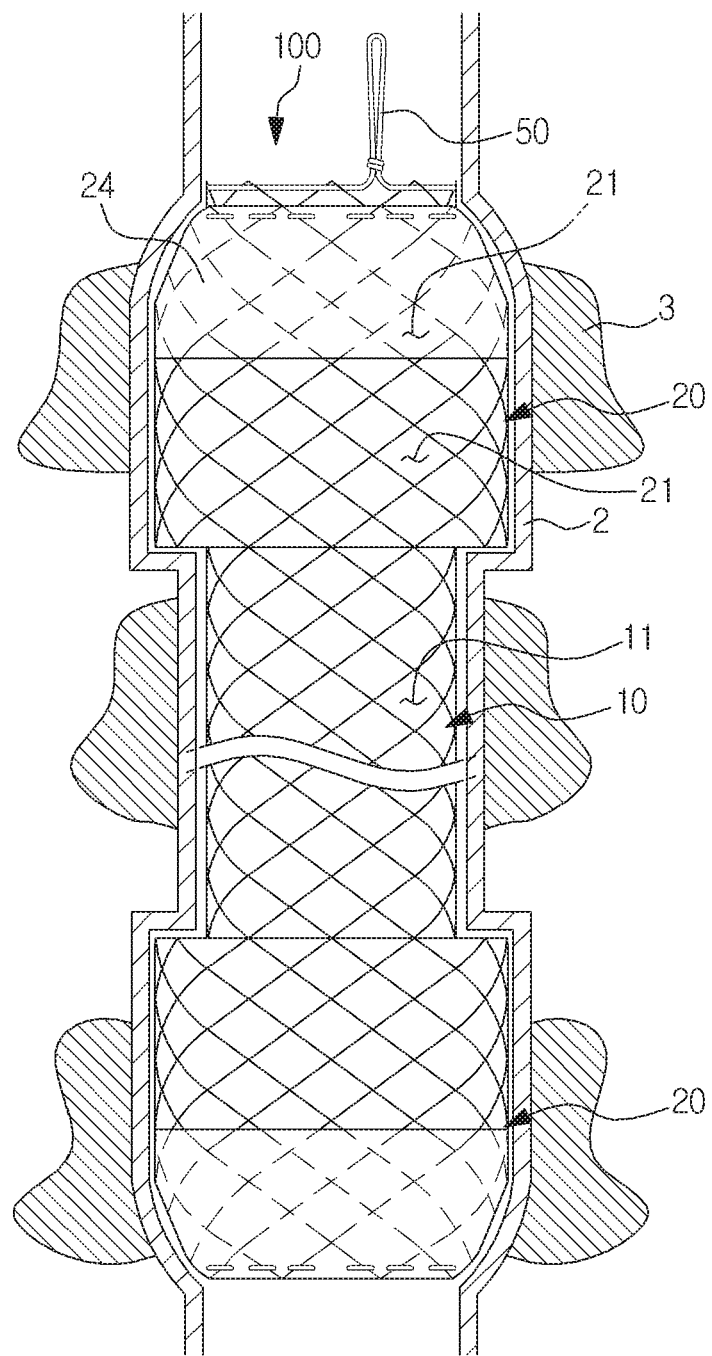
[FIG. 11A]

[FIG. 11B]
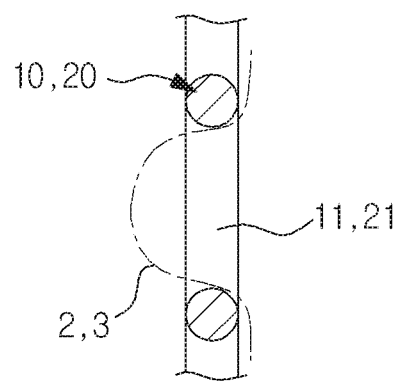
[FIG. 11C]
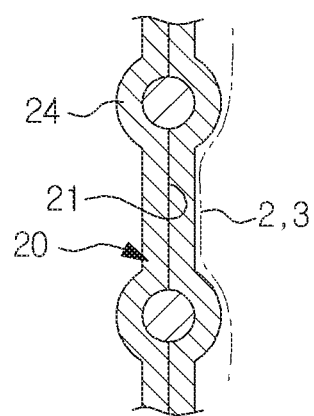

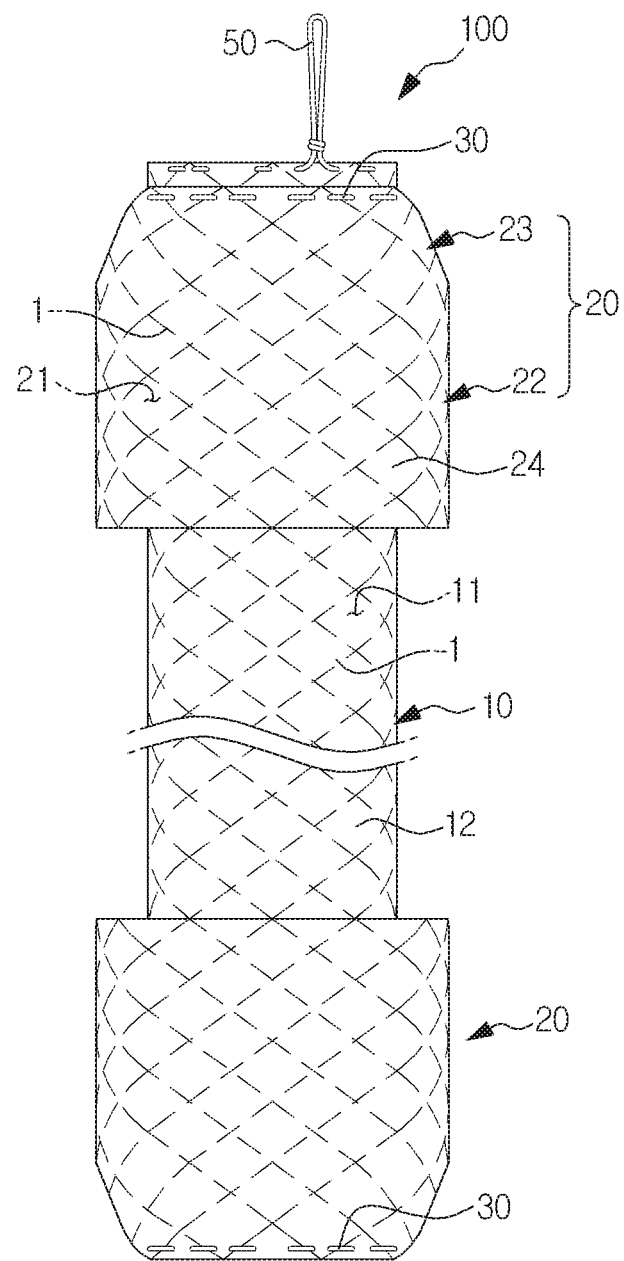
[FIG. 12A]

[FIG. 12B]
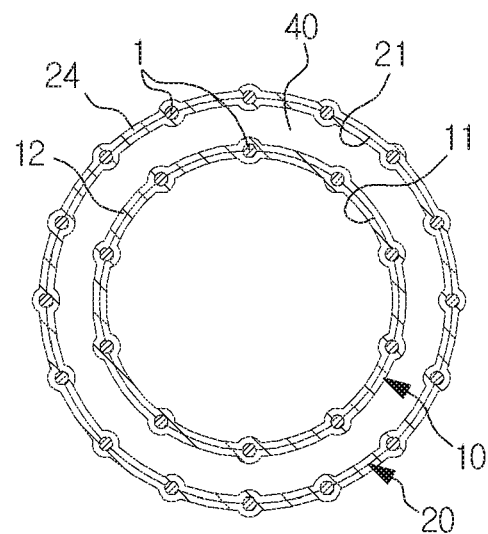
[FIG. 12C]
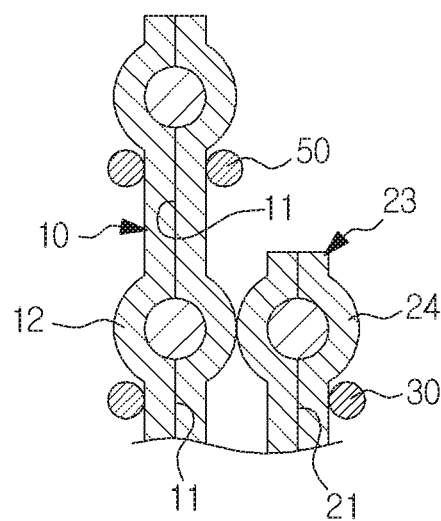

[FIG. 13A]
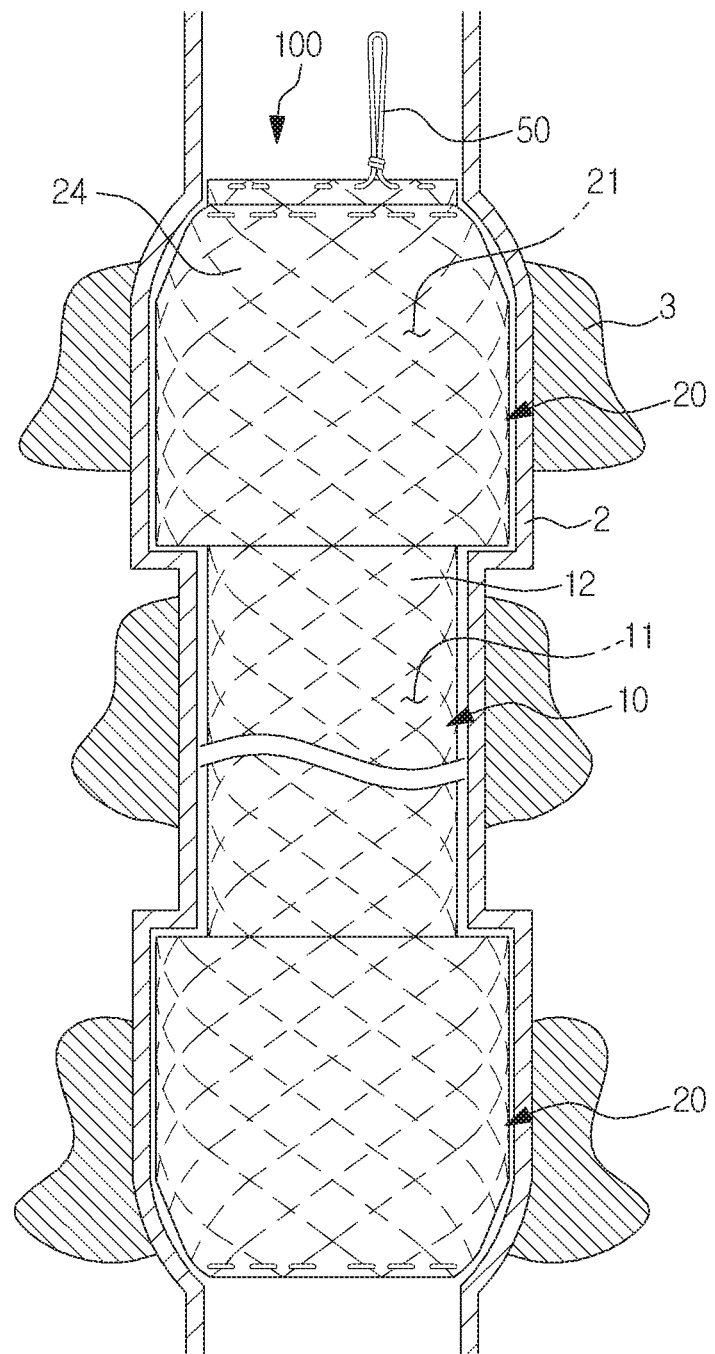

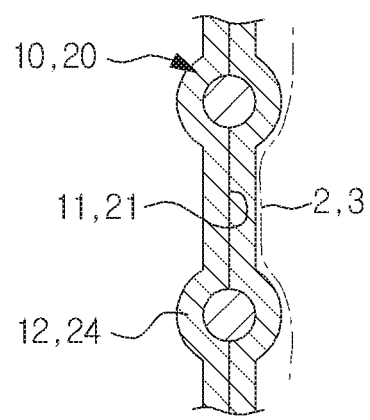
[FIG. 13B]

[FIG. 14A]
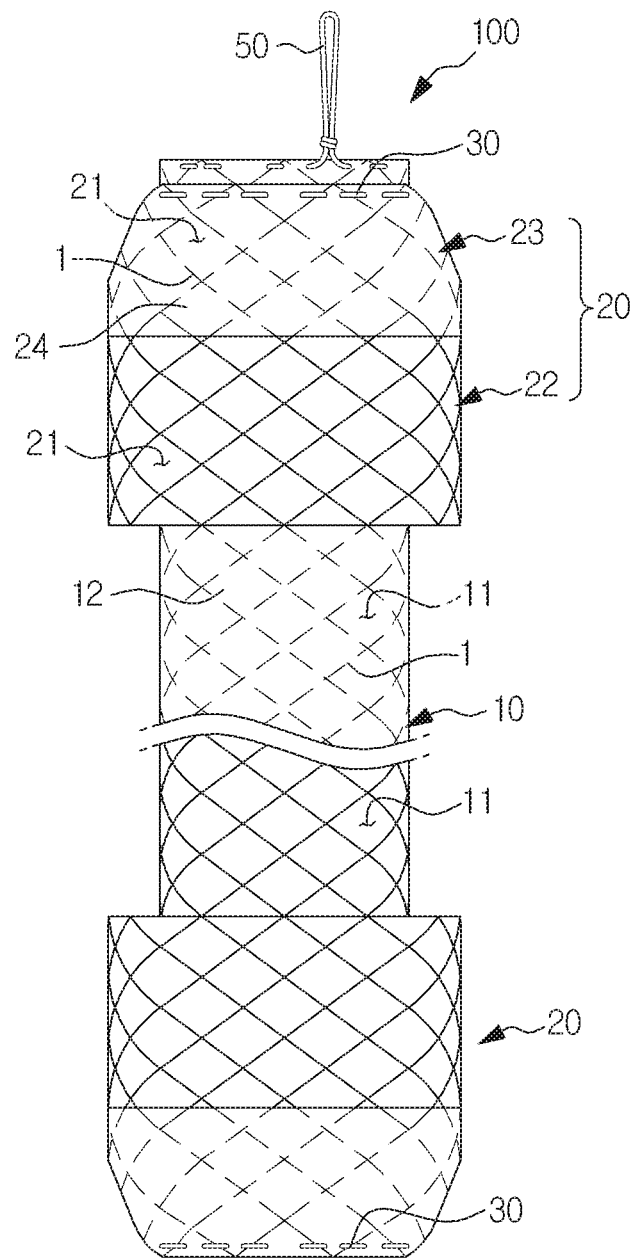

[FIG. 14B]
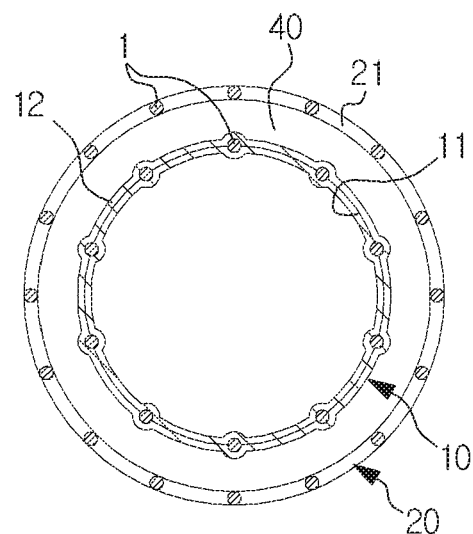
[FIG. 14C]
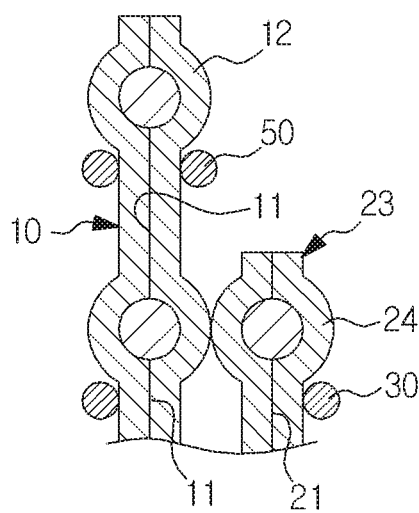

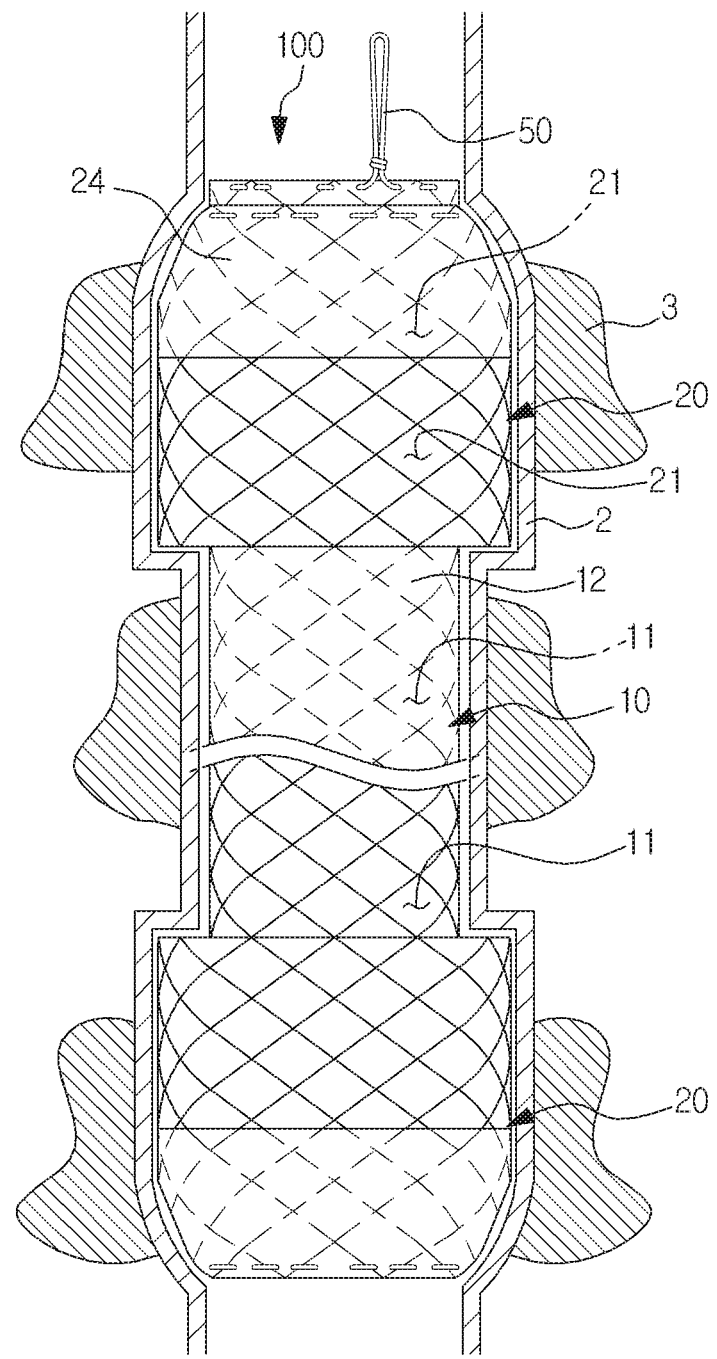
[FIG. 15A]

[FIG. 15B]
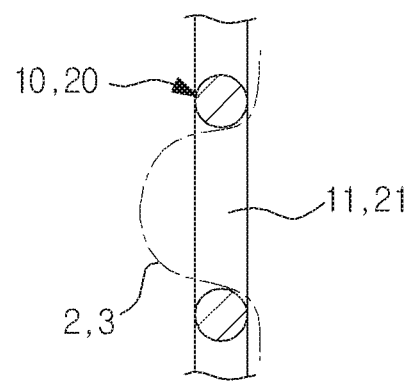
[FIG. 15C]
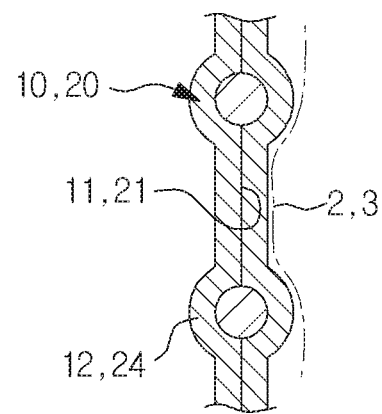

[FIG. 16A]
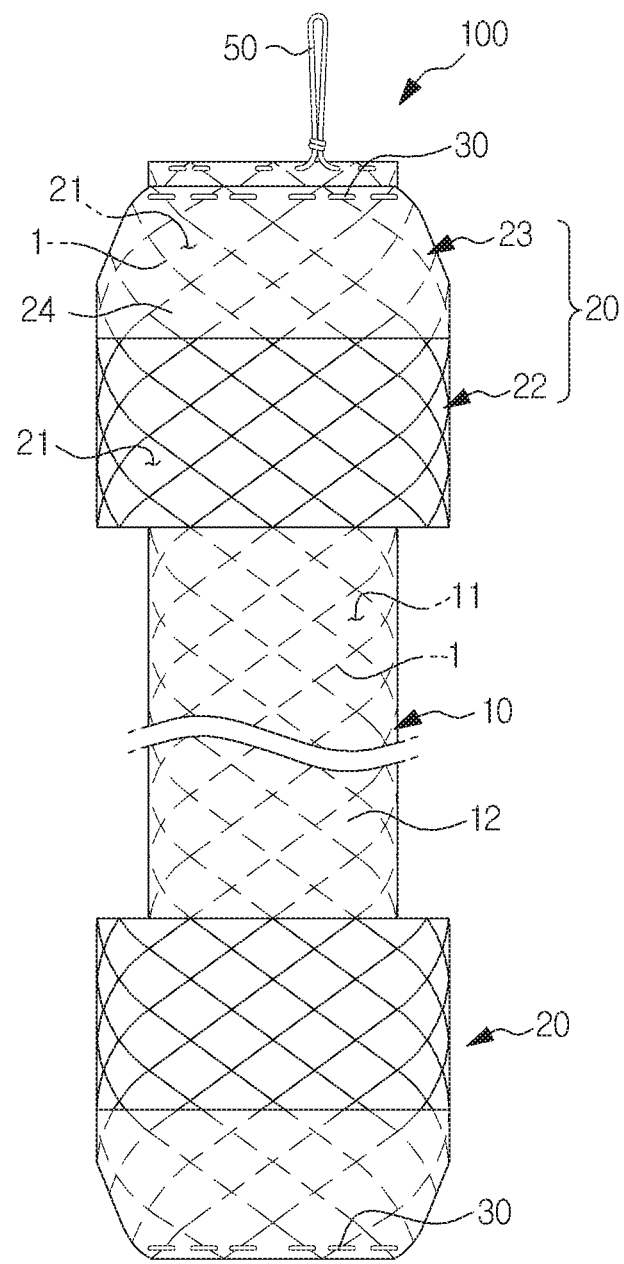

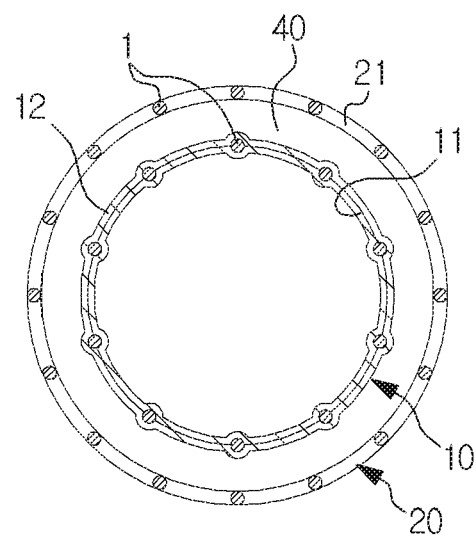
[FIG. 16B]
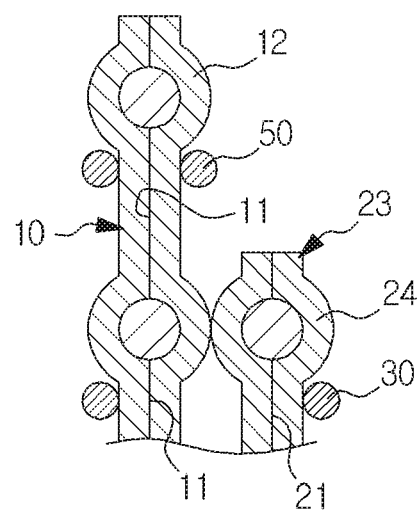
[FIG. 16C]

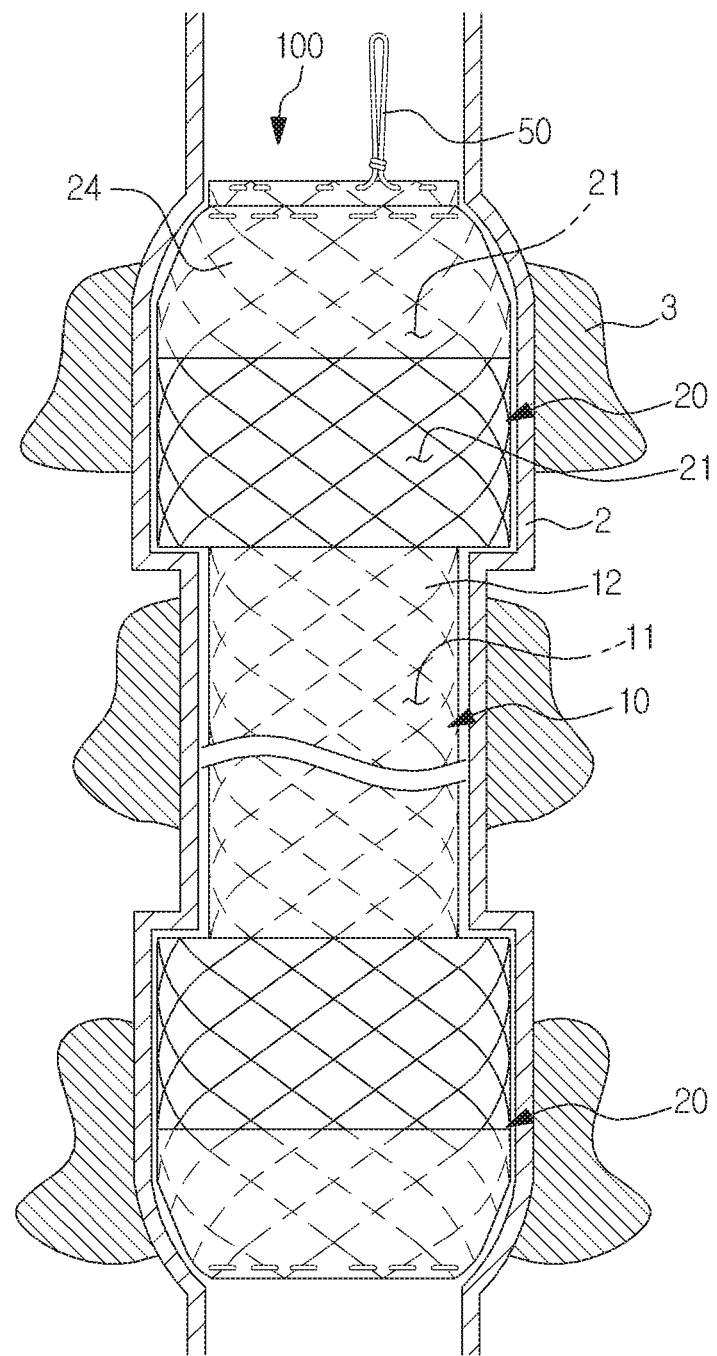
[FIG. 17A]

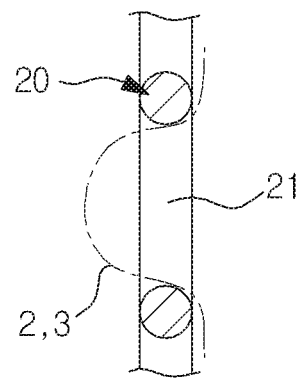
[FIG. 17B]
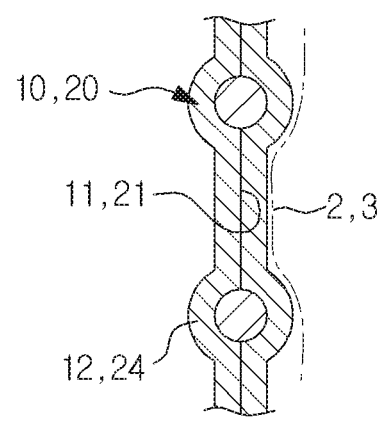
[FIG. 17C]

[FIG. 18A]
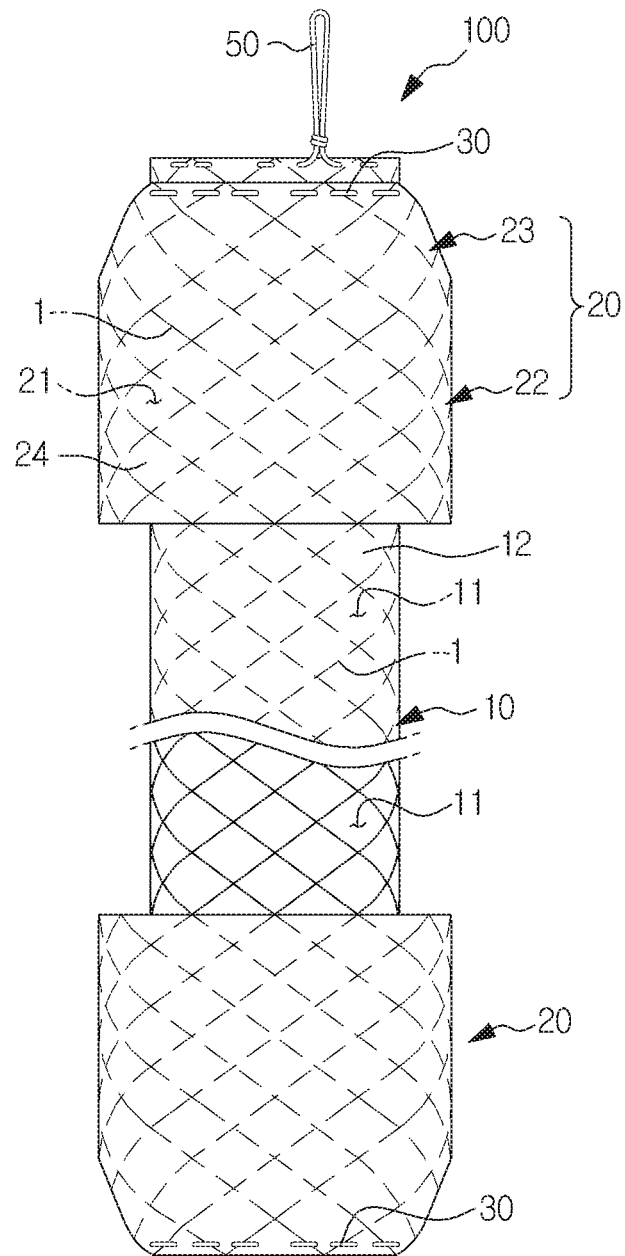

[FIG. 18B]
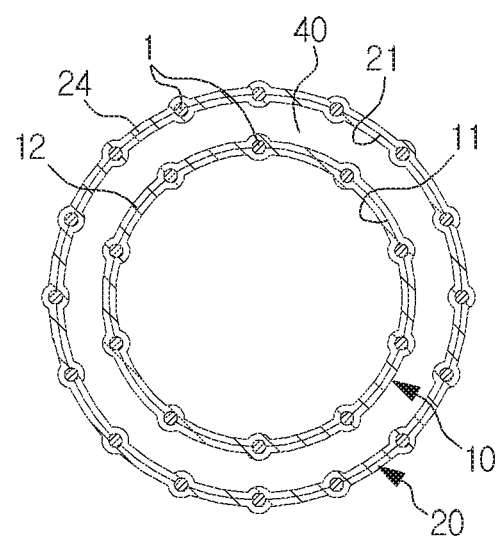
[FIG. 18C]
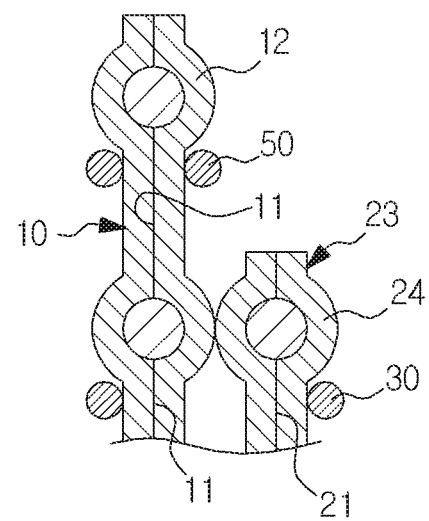

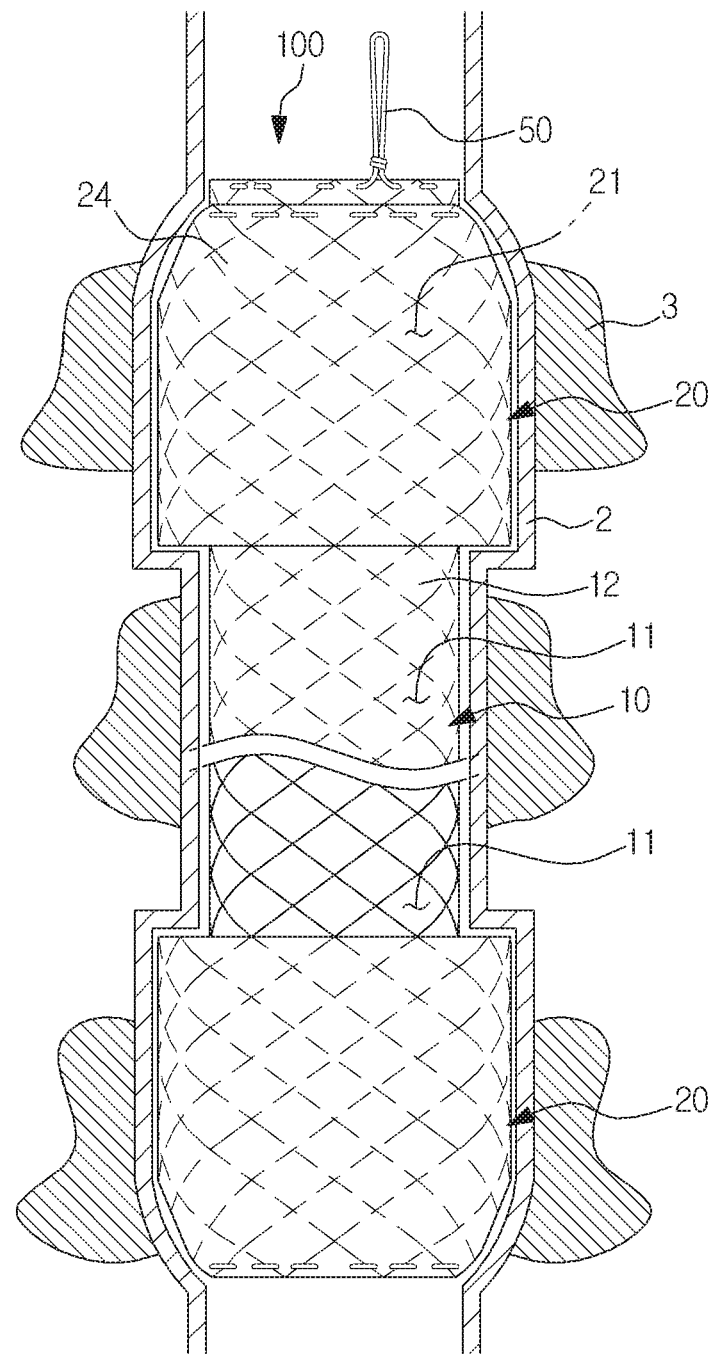
[FIG. 19A]

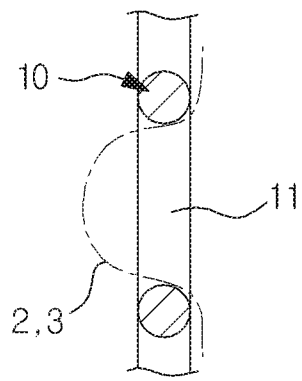
[FIG. 19B]
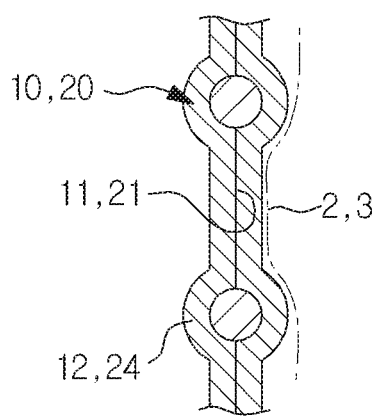
[FIG. 19C]

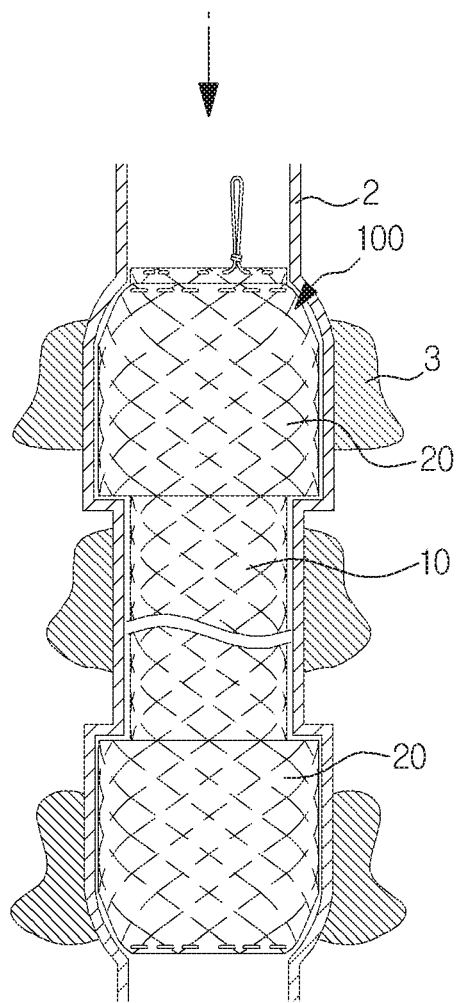
[FIG. 20A]

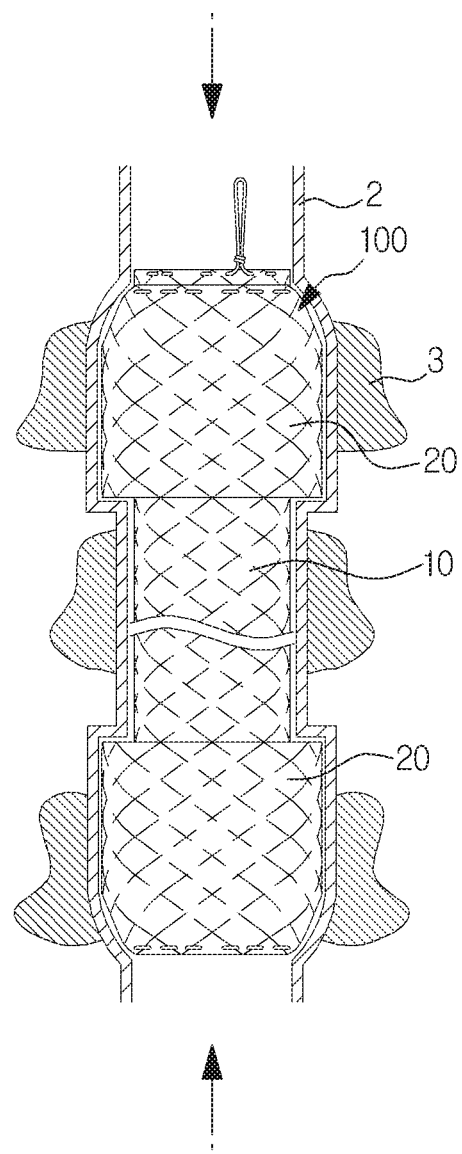
[FIG. 20B]

[FIG. 21]
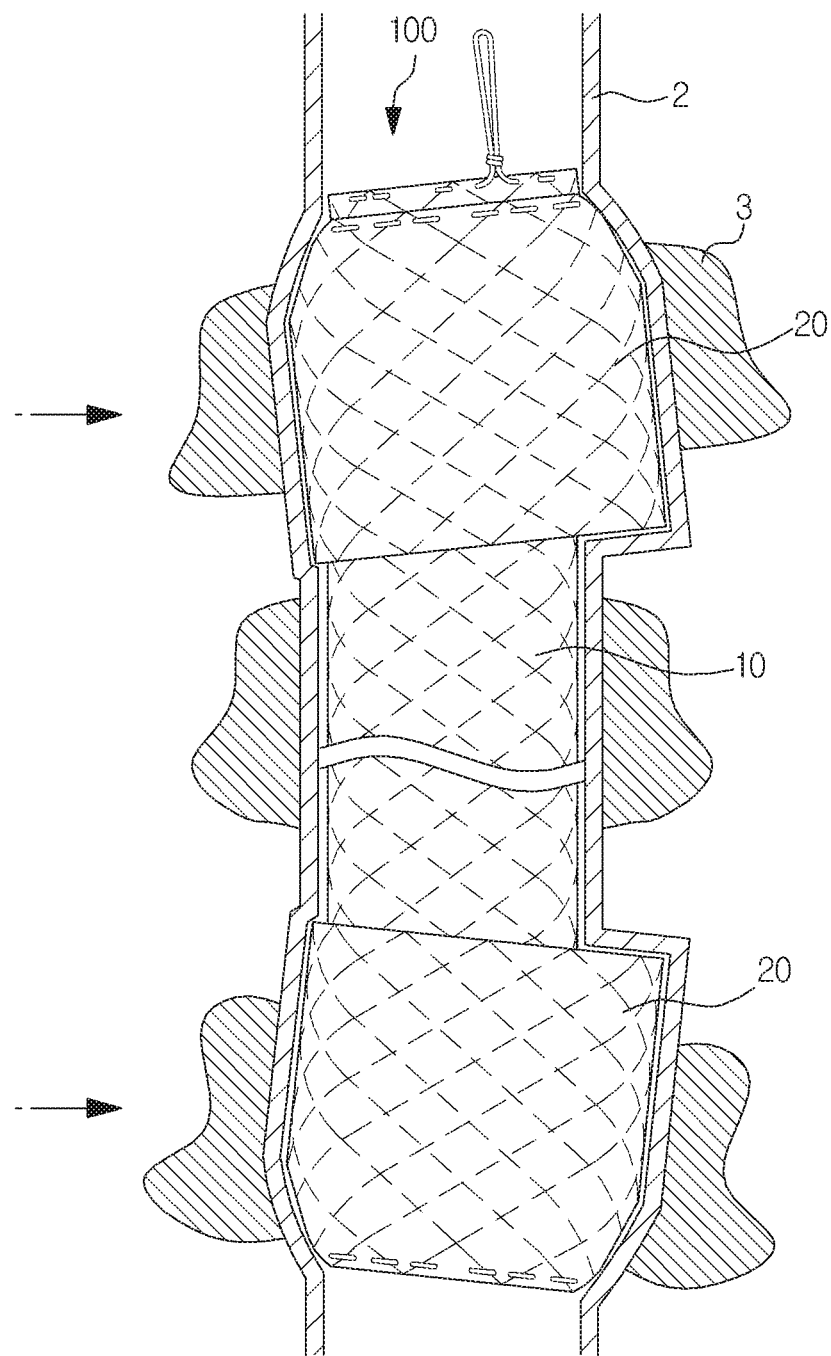

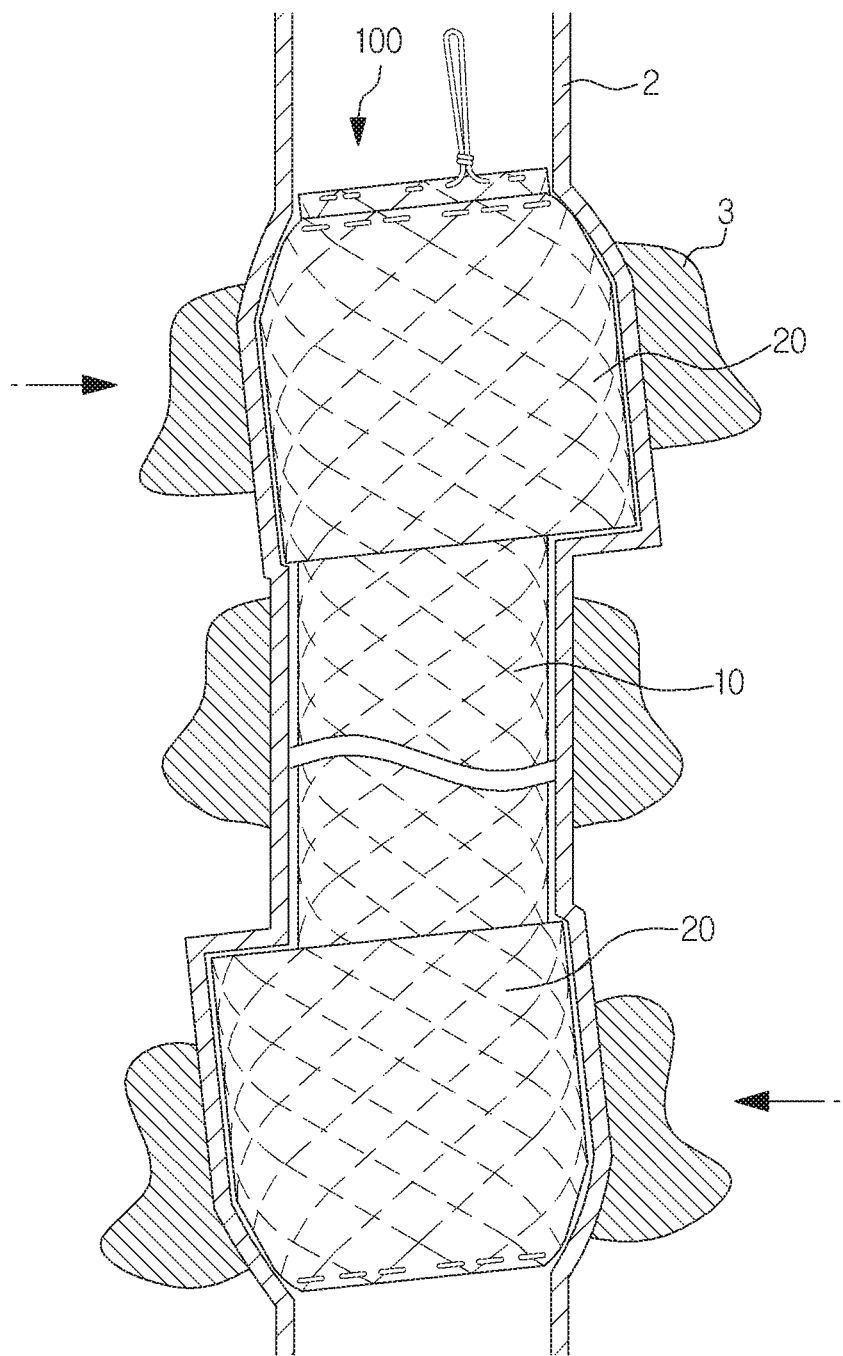
[FIG. 22]

[FIG. 23A]
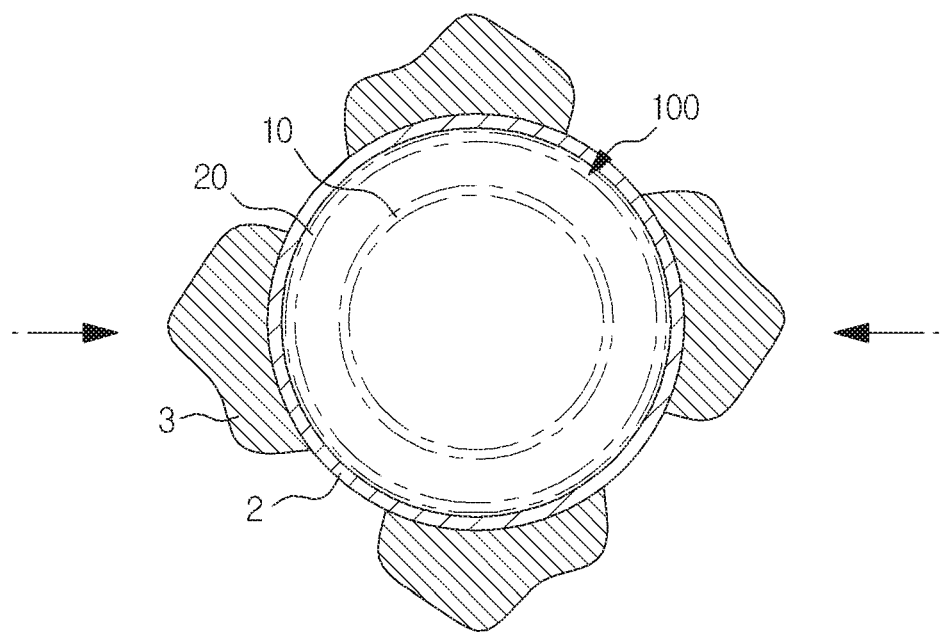
[FIG. 23B]
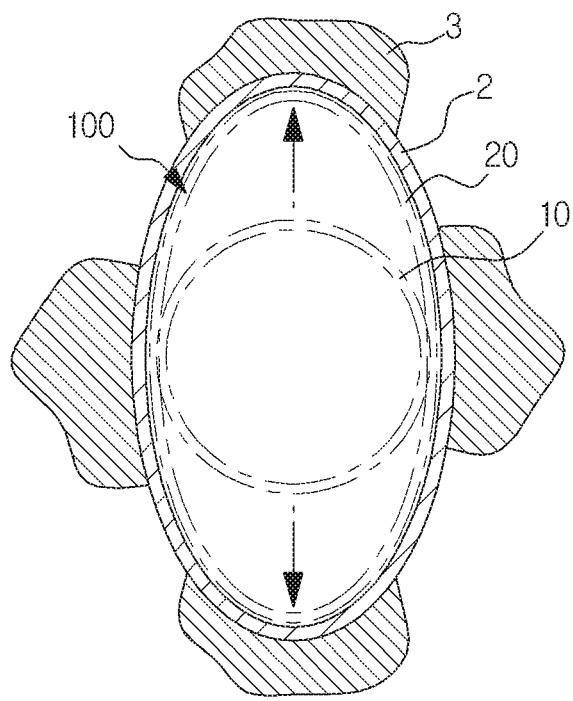

STENT

CROSS REFERENCE TO RELATED APPLICATION

The present application claims priority to Korean Patent Application No. 10-2019-0038647, filed Apr. 2, 2019, the entire contents of which is incorporated herein for all purposes by this reference.

BACKGROUND OF THE INVENTION

Field of the Invention

The present invention relates to a stent that enlarges a narrowed or occluded lesion in lumens in a body, and more particularly, to a stent having an improved anti-sliding function not to slide in a lesion even if a human body is shaken or external force is applied to a human body vertically and horizontally, that is, in all directions from the outside.

Description of the Related Art

In general, when a lesion that is narrowed or occluded by a tumor or other reasons is generated in lumens in a body such as the respiratory tract, the esophagus, the duodenum, the biliary tract, and the urethral canal, the organs cannot normally work. Accordingly, a stent is inserted into a lesion generated in a lumen in a body, whereby the lesion is expanded and the lumen can normally work.

Such a stent has a hollow cylindrical body having a plurality of diamond-shaped spaces by weaving superelastic shape memory alloy wires diagonally to cross over and under each other.

However, since such a stent has a simple hollow cylindrical body, there is a problem that the stent easily slides out of a lesion due to actions such as a cough or intake of food.

Accordingly, there is Patent Document 1, which relates to a stent for the biliary tract that can expand a narrowed biliary tract by being inserted in the biliary tract. The stent for the biliary tract has a plurality of locking ends extending at an angle outward from the body thereof and spaced apart from each other, so one or more locking ends extending from the body are locked in the biliary tract, whereby the stent can be prevented from sliding in the biliary tract.

Further, there is Patent Document 2, which relates to a stent having a hollow body having several diamond-shaped spaces by weaving at least one or more superelastic shape memory alloy wires diagonally to cross over and under each other as upper lines and lower lines. According to the stent, locking protrusions are formed on the hollow body by perpendicularly diagonally bending the wire so that the stent does not slide in a lumen. Further, the locking protrusions are formed by perpendicularly diagonally bending the upper lines of the wires with respect to the body, the upper lines go over the lower lines, that is, two or more lower lines, and two or more locking protrusions are continuously formed.

However, according to Patent Document 1, there is concern that the stent may slide in a lesion due to bending of the locking ends by shaking of a human body or an external force.

Further, even in Patent Document 2, there is concern that the stent may slide in a lesion due to bending of the locking protrusions by shaking of a human body or an external force.

Documents of Related Art
(Patent Document 1) Korean Patent No. 10-1171075
(Patent Document 2) Korean Patent No. 10-1657648

SUMMARY OF THE INVENTION

Accordingly, an objective of the present invention is to provide a stent having an improved anti-sliding function that prevents the stent from sliding in a lesion even if a human body is shaken or external force is applied to a human body vertically and horizontally, that is, in all directions.

In order to achieve the objectives of the present invention, a stent having an improved anti-sliding function includes inner and outer stents that have undergone heat treatment and have several spaces formed by weaving or crossing wires made of a superelastic shape memory alloy in a hollow cylindrical net shape, in which the outer stent is shorter than the inner stent and has an enlarged section having a diameter larger than the inner stent and a bending section formed by bending inward a side of the enlarged section; and a pair of outer stents are fitted on both ends of the inner stent such that a pair of enlarged sections face each other, and spaces of the inner stent and spaces of the bending sections are connected by connection threads, whereby a space is defined between the inner stent and the outer stent.

According to the stent of the present invention, the pair of outer stents are stuck to a lumen and a lesion in a human body, so there is an effect that the stent is less bent by shaking of the human body and external force in comparison to the related art.

That is, there is an effect that the stent is prevented from sliding in a lesion.

Further, since the pair of enlarged sections face each other, there is an effect even if shaking of a human body and external force are strongly transmitted in any one or both of vertical directions of the human body, the stent is prevented from sliding by inclined bending sections.

That is, there is an effect that even if shaking of a human body and external force are transmitted to the stent in any directions of vertical directions of a human body, one or all of the pair of enlarged sections are stuck to a lumen and a lesion in a human body.

Further, there is an effect that even if shaking of a human body and external force are transmitted to the stent in any directions of horizontal directions of a human body, the space defined between the outer stent and the inner stent is correspondingly deformed and the outer stent is stuck in a lumen and a lesion in a human body.

According to the present invention, there is an effect that when a membrane made of silicon or PTFE is not disposed on the inner and outer stents, most parts of the inner and outer stents are stuck to portions of a lumen and a lesion of a human body that are inserted in the space.

Further, when a membrane made of silicon or PTFE is disposed only on the inner stent, there is an effect that most parts of the outer stent are stuck and most parts of the inner stent are not stuck to portions of a lumen and a lesion of a human body that are inserted in the space.

Further, when a membrane made of silicon or PTFE is disposed at a predetermined portion or positions with predetermined gaps on the inner stent, there is an effect that a portion of the inner stent is stuck and most parts of the outer stent are stuck to portions of a lumen and a lesion of a human body that are inserted in the space.

Further, when a membrane made of silicon or PTFE is disposed only on the outer stent, there is an effect that most parts of the inner stent are stuck and most part of the outer stent are not stuck to portions of a lumen and a lesion of a human body that are inserted in the space.

Further, when a membrane made of silicon or PTFE is disposed at a predetermined portion or positions with predetermined gaps on the outer stent, there is an effect that a portion of the outer stent is stuck and most parts of the inner stent are stuck to portions of a lumen and a lesion of a human body that are inserted in the space.

According to the present invention, there is an effect that when a membrane made of silicon or PTFE is disposed on the inner and outer stents, portions of lumen and a lesion of a human body are not inserted in the space and most parts of the inner and outer stents are not stuck.

Further, when a membrane made of silicon or PTFE is disposed at a predetermined portion or positions with predetermined gaps on the inner and outer stents, there is an effect that portions of the inner and outer stents are stuck to portions of a lumen and a lesion of a human body that are inserted in the space.

Further, when a membrane made of silicon or PTFE is disposed on the inner stent and disposed at a predetermined portion or positions with predetermined gaps on the outer stent, there is an effect that portions of a lumen and a lesion of a human body are not inserted in the space, most parts of the inner stent are not stuck, and a portion of the outer stent is stuck to portions of the lumen and the lesion of the human body that are inserted in the space.

Further, when a membrane made of silicon or PTFE is disposed on the outer stent and disposed at a predetermined portion or positions with predetermined gaps on the inner stent, there is an effect that portions of a lumen and a lesion a human body are not inserted in the space, most parts of the outer stent are not stuck, and a portion of the inner stent is stuck to portions of the lumen and the lesion of the human body that are inserted in the space.

Further, there is an effect that the elasticity of the stent depends on whether a membrane made of silicon or PTFE is disposed.

That is, there is an effect that it is possible to adjust the degree of stimulation that is applied to a lumen of a human body.

In other words, there is an effect that it is possible to provide a stent in accordance with the conditions of patients.

According to the present invention, there is an effect that air, body fluid, or food easily moves along the membrane made of silicon or PTFE.

According to the present invention, since a pulling string is threaded only to the inner stent except for the outer stent, there is an effect that the volume of the stent is quickly decreased when the pulling string is pulled.

That is, there is an effect that the stent is quickly removed.

BRIEF DESCRIPTION OF THE DRAWINGS

The above and other objects, features and other advantages of the present invention will be more clearly understood from the following detailed description when taken in conjunction with the accompanying drawings, in which:

FIGS. 1 to 3B are views showing the details and the using state of a stent having an improved anti-sliding function according to a first embodiment of the present invention;

FIGS. 4A to 5C are views showing the details and the using state of a stent having an improved anti-sliding function according to a second embodiment of the present invention;

FIGS. 6A to 7C are views showing the details and the using state of a stent having an improved anti-sliding function according to a third embodiment of the present invention;

FIGS. 8A to 9C are views showing the details and the using state of a stent having an improved anti-sliding function according to a fourth embodiment of the present invention;

FIGS. 10A to 11C are views showing the details and the using state of a stent having an improved anti-sliding function according to a fifth embodiment of the present invention;

FIGS. 12A to 13B are views showing the details and the using state of a stent having an improved anti-sliding function according to sixth embodiment of the present invention;

FIGS. 14A to 15C are views showing the details and the using state of a stent having an improved anti-sliding function according to a seventh embodiment of the present invention;

FIGS. 16A to 17C are views showing the details and the using state of a stent having an improved anti-sliding function according to an eighth embodiment of the present invention;

FIGS. 18A to 19C are views showing the details and the using state of a stent having an improved anti-sliding function according to a ninth embodiment of the present invention; and FIGS. 20A to 23B are views showing the using state of a stent having an improved anti-sliding function according to various embodiments of the present invention.

DETAILED DESCRIPTION OF THE INVENTION

Hereafter, various embodiments of the present invention are described in detail with reference to the accompanying drawings.

As shown in FIGS. 1 to 23B, a stent 100 having an improved anti-sliding function according to various embodiments of the present invention is used to expand a narrowed or occluded lesion in a lumen 2 in a human body by being inserted into the lumen 2 of the human body such as the respiratory tract and the esophagus.

As shown in FIGS. 1 to 3B, a stent 100 according to a first embodiment of the present invention includes inner and outer stents 10 and 20 that have undergone heat treatment and have several spaces 11 and 22 formed by weaving or crossing wires 1 made of a superelastic shape memory alloy in a hollow cylindrical net shape.

The outer stent 20 is shorter in longitudinal direction than the inner stent 10.

The outer stent has a cylindrical enlarged section 22 having a larger diameter than the inner stent 10 and a conical bending section 23 formed by bending inward a side of the enlarged section 22.

In the stent 100, a pair of outer stents 20 are fitted on both ends of the inner stent 10 such that a pair of enlarged sections 22 face each other.

The pair of enlarged sections 22 of the pair of outer stents 20 face each other with an end of each of a bending sections 23 in close contact with the inner stent 10.

The pair of outer stents 20 are positioned at both ends of the inner stent 10 farthest from the center of the inner stent 10.

An end of the inner stent 10 is exposed through the bending section 23 of one outer stent 20.

In the stent 10, spaces 11 being in close contact with each other of the inner stent 10 and spaces 21 of the pair of bending sections 23 are connected by connection threads that are not harmful to a human body.

A space 40 is defined between the inner stent 10 and the outer stents 20.

In the stent 100, a pulling string 50 that is not harmful to a human body is threaded to the spaces 11 at an end of the inner stent exposed through the outer stent 20, and protrudes out of the inner stent 10.

Accordingly, the stent 100 is inserted into a narrowed or occluded lesion 3 in a lumen 2 in a human body such as the respiratory tract and the esophagus for an operation by a stent operation device such as a catheter.

Accordingly, the inner stent 10 and the pair of outer stents 20 expand the narrowed or occluded lesion 3.

Further, the pair of outer stents 20 are further inserted into the lumen 2 and the lesion 3 in the human body than the inner stent 10 and then stuck thereto.

The lumen 2 and the lesion 3 in the human body are partially inserted in the spaces 11 and 21 of the inner stent 10 and the pair of outer stents 20.

That is, the spaces 11 and 21 are stuck to portions of the lumen 2 and the lesion 3 in the human body.

Accordingly, the stent 10 is fixed in the lumen 2 and the lesion 3 in the human body.

Further, as shown in FIGS. 4A to 5C, a stent 100 according to a second embodiment that has the almost the same configuration as the first embodiment of the present invention has a membrane 12 made of silicon or Polytetrafluoroethylene (PTFE) on the inner stent 10, so the spaces 11 are covered.

Accordingly, the stent 100 is inserted into a narrowed or occluded lesion 3 in a lumen 2 in a human body such as the respiratory tract and the esophagus for an operation by a stent operation device such as a catheter.

Accordingly, the inner stent 10 and the pair of outer stents 20 expand the narrowed or occluded lesion 3.

Further, the pair of outer stents 20 are further inserted into the lumen 2 and the lesion 3 in the human body than the inner stent 10 and then stuck thereto.

The lumen 2 and the lesion in the human body partially inserted in the spaces 21 of the pair of outer stents 20.

That is, the spaces 21 are stuck to portions of the lumen 2 and the lesion 3 in the human body.

The spaces 11 of the inner stent 10 are covered by the membrane 12, so the lumen 2 and the lesion 3 in the human body are not inserted therein.

Accordingly, the stent 10 is fixed in the lumen 2 and the lesion 3 in the human body.

Further, as shown in FIGS. 6A to 7C, a stent 100 according to a third embodiment that has the almost the same configuration as the first embodiment of the present invention has a membrane 12 made of silicon or Polytetrafluoroethylene (PTFE) at a predetermined portion or at positions with predetermined gaps on the inner stent 10, so only some of the spaces 11 are covered.

Accordingly, the stent 100 is inserted into a narrowed or occluded lesion 3 in a lumen 2 in a human body such as the respiratory tract and the esophagus for an operation by a stent operation device such as a catheter.

Accordingly, the inner stent 10 and the pair of outer stents 20 expand the narrowed or occluded lesion 3.

Further, the pair of outer stents 20 are further inserted into the lumen 2 and the lesion 3 in the human body than the inner stent 10 and then stuck thereto.

The lumen 2 and the lesion in the human body partially inserted in the spaces 21 of the pair of outer stents 20.

That is, the spaces 21 are stuck to portions of the lumen 2 and the lesion 3 in the human body.

Some of the spaces 11 of the inner stent 10 are not covered by the membrane 12, so the lumen 2 and the lesion 3 in the human body are inserted therein.

That is, the spaces 11 are stuck to portions of the lumen 2 and the lesion 3 in the human body.

The others of the spaces 11 of the inner stent 10 are covered by the membrane 12, so the lumen 2 and the lesion 3 in the human body are not inserted therein.

Accordingly, the stent 10 is fixed in the lumen 2 and the lesion 3 in the human body.

Further, as shown in FIGS. 8A to 9C, a stent 100 according to a fourth embodiment that has the almost the same configuration as the first embodiment of the present invention has a membrane 24 made of silicon or Polytetrafluoroethylene (PTFE) on the outer stent 20, so the spaces 21 are covered.

Accordingly, the stent 100 is inserted into a narrowed or occluded lesion 3 in a lumen in a human body such as the respiratory tract and the esophagus for an operation by a stent operation device such as a catheter.

Accordingly, the inner stent 10 and the pair of outer stents 20 expand the narrowed or occluded lesion 3.

Further, the pair of outer stents 20 are further inserted into the lumen 2 and the lesion 3 in the human body than the inner stent 10 and then stuck thereto.

The lumen 2 and the lesion in the human body partially inserted in the spaces 11 of the inner stent 10.

That is, the spaces 11 are stuck to portions of the lumen 2 and the lesion 3 in the human body.

The spaces 21 of the outer stent 20 are covered by the membrane 24, so the lumen 2 and the lesion 3 in the human body are not inserted therein.

Accordingly, the stent 10 is fixed in the lumen 2 and the lesion 3 in the human body.

Further, as shown in FIGS. 10A to 11C, a stent 100 according to a fifth embodiment that has the almost the same configuration as the first embodiment of the present invention has a membrane 24 made of silicon or Polytetrafluoroethylene (PTFE) at a predetermined portion or at positions with predetermined gaps on the outer stent 20, so only some of the spaces 21 are covered.

Accordingly, the stent 100 is inserted into a narrowed or occluded lesion 3 in a lumen 2 in a human body such as the respiratory tract and the esophagus for an operation by a stent operation device such as a catheter.

Accordingly, the inner stent 10 and the pair of outer stents 20 expand the narrowed or occluded lesion 3.

Further, the pair of outer stents 20 are further inserted into the lumen 2 and the lesion 3 in the human body than the inner stent 10 and then stuck thereto.

The lumen 2 and the lesion in the human body partially inserted in the spaces 11 of the inner stent 10.

That is, the spaces 11 are stuck to portions of the lumen 2 and the lesion 3 in the human body.

Some of the spaces 21 of the outer stent 20 are not covered by the membrane 24, so the lumen 2 and the lesion 3 in the human body are inserted therein.

That is, the spaces 21 are stuck to portions of the lumen 2 and the lesion 3 in the human body.

The others of the spaces 21 of the outer stent 20 are covered by the membrane 24, so the lumen 2 and the lesion 3 in the human body are not inserted therein.

Accordingly, the stent 10 is fixed in the lumen 2 and the lesion 3 in the human body.

Further, as shown in FIGS. 12A to 13B, a stent 100 according to a sixth embodiment that has the almost the same configuration as the first embodiment of the present invention has membranes 12 and 24 made of silicon or Polytetrafluoroethylene (PTFE) on the inner and outer stents 10 and 20, so the spaces 11 and 21 are covered.

Accordingly, the stent 100 is inserted into a narrowed or occluded lesion 3 in a lumen in a human body such as the respiratory tract and the esophagus for an operation by a stent operation device such as a catheter.

Accordingly, the inner stent 10 and the pair of outer stents 20 expand the narrowed or occluded lesion 3.

Further, the pair of outer stents 20 are further inserted into the lumen 2 and the lesion 3 in the human body than the inner stent 10 and then stuck thereto.

The spaces 11 and 21 of the inner and outer stents 10 and 20 are covered by the membranes 12 and 24, so the lumen 2 and the lesion 3 in the human body are not inserted therein.

Accordingly, the stent 10 is fixed in the lumen 2 and the lesion 3 in the human body.

Further, as shown in FIGS. 14A to 15C, a stent 100 according to a seventh embodiment that has the almost the same configuration as the first embodiment of the present invention has membranes 12 and 24 made of silicon or Polytetrafluoroethylene (PTFE) at a predetermined portion or at positions with predetermined gaps on inner and outer stent 10 and 20, so only some of the spaces 11 and 21 are covered.

Accordingly, the stent 100 is inserted into a narrowed or occluded lesion 3 in a lumen 2 in a human body such as the respiratory tract and the esophagus for an operation by a stent operation device such as a catheter.

Accordingly, the inner stent 10 and the pair of outer stents 20 expand the narrowed or occluded lesion 3.

Further, the pair of outer stents 20 are further inserted into the lumen 2 and the lesion 3 in the human body than the inner stent 10 and then stuck thereto.

Some of the spaces 11 and 21 of the inner and outer stent 10 and 20 are not covered by the membranes 12 and 24, so the lumen 2 and the lesion 3 in the human body are inserted therein.

That is, the spaces 11 and 21 are stuck to portions of the lumen 2 and the lesion 3 in the human body.

The others of the spaces 11 and 21 of the inner and outer stents 10 and 20 are covered by the membranes 12 and 24, so the lumen 2 and the lesion 3 in the human body are not inserted therein.

Accordingly, the stent 10 is fixed in the lumen 2 and the lesion 3 in the human body.

Further, as shown in FIGS. 16A to 17C, a stent 100 according to an eighth embodiment that has the almost the same configuration as the first embodiment of the present invention has a membrane 12 made of silicon or Polytetrafluoroethylene (PTFE) on the inner stent 10, so the spaces 11 and 21 are covered.

Further, in the stent 100, a membrane 24 made of silicon or Polytetrafluoroethylene (PTFE) is formed only at a predetermined portion or positions with predetermined gaps on the outer stent 20, so only some of the spaces 21 are covered.

Accordingly, the stent 100 is inserted into a narrowed or occluded lesion 3 in a lumen in a human body such as the respiratory tract and the esophagus for an operation by a stent operation device such as a catheter.

Accordingly, the inner stent 10 and the pair of outer stents 20 expand the narrowed or occluded lesion 3.

Further, the pair of outer stents 20 are further inserted into the lumen 2 and the lesion 3 in the human body than the inner stent 10 and then stuck thereto.

Some of the spaces 21 of the outer stent 20 are not covered by the membrane 24, so the lumen 2 and the lesion 3 in the human body are inserted therein.

That is, the spaces 21 are stuck to portions of the lumen 2 and the lesion 3 in the human body.

The others of the spaces 11 of the inner stent 10 and the spaces 21 of the outer stent 20 are covered by the membranes 12 and 24, so the lumen 2 and the lesion 3 in the human body are not inserted therein.

Accordingly, the stent 10 is fixed in the lumen 2 and the lesion 3 in the human body.

Further, as shown in FIGS. 18A to 19C, a stent 100 according to a ninth embodiment that has the almost the same configuration as the first embodiment of the present invention has a membrane 12 made of silicon or Polytetrafluoroethylene (PTFE) at a predetermined portion or at positions with predetermined gaps on the inner stent 10, so only some of the spaces 11 are covered.

Further, in the stent 100, a membrane 24 made of silicon or Polytetrafluoroethylene (PTFE) is formed on the outer stent 20, so the spaces 21 are covered.

Accordingly, the stent 100 is inserted into a narrowed or occluded lesion 3 in a lumen in a human body such as the respiratory tract and the esophagus for an operation by a stent operation device such as a catheter.

Accordingly, the inner stent 10 and the pair of outer stents 20 expand the narrowed or occluded lesion 3.

Further, the pair of outer stents 20 are further inserted into the lumen 2 and the lesion 3 in the human body than the inner stent 10 and then stuck thereto.

Some of the spaces 11 of the inner stent 10 are not covered by the membrane 12, so the lumen 2 and the lesion 3 in the human body are inserted therein.

That is, the spaces 11 are stuck to portions of the lumen 2 and the lesion 3 in the human body.

The others of the spaces 21 of the outer stent 20 and the spaces 11 of the inner stent 10 are covered by the membranes 12 and 24, so the lumen 2 and the lesion 3 in the human body are not inserted therein.

Accordingly, the stent 10 is fixed in the lumen 2 and the lesion 3 in the human body.

Further, as shown in FIGS. 20A and 20B, the pair of outer stents 20 of the stent 100 according to various embodiments of the present invention are stuck to the lumen 2 and the lesion 3 in the human body when the outer stents 20 receive shaking of the human body and external force applied to the human in perpendicular direction of the human body.

That is, when the pair of outer stents 20 of the stent 100 strongly receive shaking of the human body and external force applied to the human in any one or both of perpendicular directions of the human body, the outer stents 20 can slide in the lesion 3, but the pair of enlarged sections 22 face each other, so one or both of the enlarged sections 22 are stuck to the lumen 2 and the lesion 3.

In other words, the stent 100 does not slide in the lesion 3.

Further, as shown in FIG. 21, the pair of outer stents 2 of the stent 100 according to various embodiments of the present invention are pressed in the same direction to the lumen 2 and the lesion 3 in the human body when the outer stents 20 receive shaking of the human body and external force applied to the human in any one of horizontal directions of the human body.

Then, the space 40 defined between the inner stent 10 and the pair of outer stents 20 is deformed and the pair of outer stents 20 are inclined together in any one direction with respect to the inner stent 10.

The inclined outer stents 20 are stuck while being inserted deeper in the lumen 2 and lesion 3 in the human body.

That is, the stent 100 does not slide in the lesion 3.

Further, as shown in FIG. 22, the pair of outer stents 20 of the stent 100 according to various embodiments of the present invention are pressed in different directions to the lumen 2 and the lesion 3 in the human body when the outer stents 20 receive shaking of the human body and external force applied to the human in different horizontal directions of the human body.

Then, the space 40 defined between the inner stent 10 and the pair of outer stents 20 is deformed and the pair of outer stents 20 are inclined different directions with respect to the inner stent 10.

The inclined outer stents 20 are stuck while being inserted deeper in the lumen 2 and lesion 3 in the human body.

That is, the stent 100 does not slide in the lesion 3.

Further, as shown in FIG. 23, the pair of outer stents 21 of the stent 100 according to various embodiments of the present invention are pressed in the same direction to the lumen 2 and the lesion 3 in the human body when the outer stents 21 receive together shaking of the human body and external force applied to the human in any one of horizontal directions of the human body.

Then, the space 40 defined between the inner stent 10 and the pair of outer stents 20 is deformed and both non-pressed sides of the pair of outer stents 20 protrude toward the lumen 2 and the lesion 3 in the human body with respect to the inner stent 10.

The both protruding sides of the pair of outer stents 20 are stuck while being inserted deeper in the lumen 2 and lesion 3 in the human body.

That is, the stent 100 does not slide in the lesion 3.

Accordingly, when the narrowed or occluded lesion 3 in the lumen 2 of the human body is cured, a user pulls the pulling string suing a stent operation device such as a catheter.

Then, the entire stent 100 of the present invention stretches and the volume decreases, so the stent 10 is easily taken out of the lumen 2 and the human body by a stent operation device such as a catheter.

Although the present invention was described above with reference to specific embodiments, the present invention is not limited to the embodiments and may be changed and modified in various ways by those skilled in the art without departing from the scope of the present invention.

What is claimed is:

1. A stent having an improved anti-sliding function, the stent comprising an inner stent and a pair of outer stents that have undergone heat treatment and have several spaces formed by weaving or crossing wires made of a superelastic shape memory alloy in a hollow cylindrical net shape,
wherein each of the outer stents is shorter than the inner stent and has an enlarged section having a diameter larger than the inner stent and a bending section formed by bending inward a side of the enlarged section, and
the pair of outer stents are fitted on both ends of the inner stent such that the enlarged sections of the pair of outer stents face each other, and spaces of the inner stent and spaces of the bending sections of the pair of outer stents are connected by a connection thread, whereby a space section is defined between the inner stent and the outer stents.

2. The stent of claim 1, wherein a pulling string is threaded to the spaces at an end of the inner stent exposed through the bending section of each of the outer stents.

3. The stent of claim 1, wherein a membrane made of silicon or Polytetrafluoroethylene (PTFE) is disposed on the inner stent to cover the spaces of the inner stent.

4. The stent of claim 1, wherein a membrane made of silicon or Polytetrafluoroethylene (PTFE) is disposed at a predetermined portion or positions with predetermined gaps on the inner stent to cover only some of the spaces of the inner stent.

5. A stent having an improved anti-sliding function, the stent comprising an inner stent and a pair of outer stents that have undergone heat treatment and have several spaces formed by weaving or crossing wires made of a superelastic shape memory alloy in a hollow cylindrical net shape,
wherein each of the outer stents is shorter than the inner stent and has an enlarged section having a diameter larger than the inner stent and a bending section formed by bending inward a side of the enlarged section,
a membrane made of silicon or Polytetrafluoroethylene (PTFE) is disposed on each of the outer stents to cover the spaces of the outer stents, and
the pair of outer stents are fitted on both ends of the inner stent such that the enlarged sections of the pair of outer stents face each other, and spaces of the inner stent and spaces of the bending sections of the pair of outer stents are connected by a connection thread, whereby a space section is defined between the inner stent and the outer stents.

6. The stent of claim 5, wherein a pulling string is threaded to the spaces at an end of the inner stent exposed through the bending section of each of the outer stents.

7. The stent of claim 5, wherein a membrane made of silicon or Polytetrafluoroethylene (PTFE) is disposed at a predetermined portion or positions with predetermined gaps on each of the outer stents to cover only some of the spaces of the outer stents.

8. A stent having an improved anti-sliding function, the stent comprising an inner stent and a pair of outer stents that have undergone heat treatment and have several spaces formed by weaving or crossing wires made of a superelastic shape memory alloy in a hollow cylindrical net shape,
wherein each of the outer stents is shorter than the inner stent and has an enlarged section having a diameter larger than the inner stent and a bending section formed by bending inward a side of the enlarged section,
a membrane made of silicon or Polytetrafluoroethylene (PTFE) is disposed on the inner stent to cover the spaces of the inner stent and a membrane made of silicon or Polytetrafluoroethylene (PTFE) is disposed on each of the outer stents to cover the spaces of the outer stents, and
the pair of outer stents are fitted on both ends of the inner stent such that the enlarged sections of the pair of outer stents face each other, and spaces of the inner stent and spaces of the bending sections of the pair of outer stents are connected by a connection thread, whereby a space section is defined between the inner stent and the outer stents.

9. The stent of claim 8, wherein a pulling string is threaded to the spaces at an end of the inner stent exposed through the bending section of each of the outer stents.

10. The stent of claim 8, wherein a membrane made of silicon or Polytetrafluoroethylene (PTFE) is disposed at a predetermined portion or positions with predetermined gaps on the inner stent to cover only some of the spaces of the inner stent and a membrane made of silicon or Polytetrafluoroethylene (PTFE) is disposed at a predetermined portion or positions with predetermined gaps on each of the outer stents to cover only some of the spaces of the outer stents.

11. The stent of claim 8, wherein a membrane made of silicon or Polytetrafluoroethylene (PTFE) is disposed at a predetermined portion or positions with predetermined gaps on each of the outer stents to cover only some of the spaces of the outer stents.

12. The stent of claim 8, wherein a membrane made of silicon or Polytetrafluoroethylene (PTFE) is disposed at a predetermined portion or positions with predetermined gaps on the inner stent to cover only some of the spaces of the inner stent.

* * * * *